US012215132B2

(12) United States Patent
Karsenty et al.

(10) Patent No.: US 12,215,132 B2
(45) Date of Patent: Feb. 4, 2025

(54) METHODS, COMPOSITIONS AND USES THEREOF FOR REVERSING SARCOPENIA

(71) Applicants: The Trustees of Columbia University in the City of New York, New York, NY (US); William Marsh Rice University, Houston, TX (US)

(72) Inventors: Gerard Karsenty, New York, NY (US); Julian Berger, New York, NY (US); Han Xiao, Houston, TX (US)

(73) Assignees: The Trustees of Columbia University in the City of New York, New York, NY (US); William Marsh Rice University, Houston, TX (US)

( * ) Notice: Subject to any disclaimer, the term of this patent is extended or adjusted under 35 U.S.C. 154(b) by 554 days.

(21) Appl. No.: 17/504,158

(22) Filed: Oct. 18, 2021

(65) Prior Publication Data

US 2022/0106372 A1   Apr. 7, 2022

Related U.S. Application Data

(63) Continuation of application No. PCT/US2021/027942, filed on Apr. 19, 2021.

(60) Provisional application No. 63/011,956, filed on Apr. 17, 2020.

(51) Int. Cl.
*A61K 38/00* (2006.01)
*A61P 21/06* (2006.01)
*C07K 14/54* (2006.01)
*C07K 14/575* (2006.01)

(52) U.S. Cl.
CPC ............ *C07K 14/575* (2013.01); *A61P 21/06* (2018.01); *C07K 14/5412* (2013.01); *A61K 38/00* (2013.01); *C07K 2319/00* (2013.01); *C07K 2319/30* (2013.01)

(58) Field of Classification Search
CPC .................................................. A61K 38/204
See application file for complete search history.

(56) References Cited

U.S. PATENT DOCUMENTS

| | | |
|---|---|---|
| 2007/0298056 A1 | 12/2007 | Brahmbhatt et al. |
| 2017/0319660 A1 | 11/2017 | Karsenty et al. |
| 2018/0112232 A1 | 4/2018 | Rodgers et al. |
| 2019/0144856 A1 | 5/2019 | Hong et al. |
| 2019/0209474 A1 | 7/2019 | Fahmy et al. |
| 2019/0231859 A1 | 8/2019 | Franzusoff et al. |

FOREIGN PATENT DOCUMENTS

WO   WO 2014/113875 A1 *   7/2014

OTHER PUBLICATIONS

Haddad et al. (2005), J. Appl. Physiol 98: 911-917.*
Pereira et al. (2009), Archives of Gerontology and Geriatrics, 48, 313-316.*
Zhou B, et al. "Autophagic dysfunction is improved by intermittent administration of osteocalcin in obese mice" International Journal of Obesity, vol. 40 / Issue 5, pp. 833-843, May 2016.
Beduneau et al., 2008, J. Control. Release 126:44-49.
Bennett et al., 1995, J. Mol. Recog. 8:52-58.
Biocomputing: Informatics and Genome Projects, Smith, D. W., ed., Academic Press, New York, 1993.
Giuliani N, et al. "Bisphosphonates inhibit IL-6 production by human osteoblast-like cells" Scandinavian Journal of Rheumatology, vol. 27 / Issue 1, pp. 38-41, 1998.
Bundgaard, H., Advanced Drug Delivery Review, 1992, 8, pp. 1-38.
Cho et al., 1993, Science 261:1303-1305.
Watt MJ, et al. "CNTF reverses obesityinduced insulin resistance by activating skeletal muscle AMPK" Nature Medicine, vol. 12 / Issue 5, pp. 541-548, May 2006.
Computational Molecular Biology, Lesk, A. M., ed., Oxford University Press, New York, 1988.
Bowie et al., 1990, Science 247:1306-1310.
Computer Analysis of Sequence Data, Part 1, Griffin, A. M., and Griffin, HG., eds., Humana Press, New Jersey, 1994.
Crystal, 1995, Science 270:404-410.
A Ed., Elsevier, 1985; Design and Application of Prodrugs, A Textbook of Drug Design and Development, Krosgaard-Larsen and H. Bundgaard, Ed., 1991, Chapter 5, pp. 113-191.
Ducy et al., 1996, Nature 382:448-452.
Ducy et al., 2000, Science 289:1501-1504; Harada & Rodan, 2003, Nature 423:349-355.
Findeisen M, et al. "Treatment of type 2 diabetes with the designer cytokine IC7Fc" Nature, vol. 574 / Issue 7776, pp. 63-68, Oct. 2019.
Flotte et al., 1993, Proc. Natl. Acad. Sci. USA 90:10613-10617.
Friedmann, 1989, Science, 244:1275-1281; Mulligan, 1993, Science, 260:926-932.
Gene Therapy: Principles and Applications, ed. T. Blackenstein, Springer Verlag, 1999.
Gene Therapy Protocols (Methods in Molecular Medicine), ed. P. D. Robbins, Humana Press, 1997.
Harada & Rodan, 2003, Nature 423:349-355.
Hauschka et al., 1989, Physiol. Review 69:990-1047; Price, 1989, Connect. Tissue Res. 21:51-57.
Hermonat & Muzyczka, 1984, Proc. Natl. Acad. Sci. USA., 81:6466-6470.
Houghten, 1985, Proc. Natl. Acad. Sci. USA 82:5131-5135.
Pollard KM, et al. "Induction of systemic autoimmunity by a xenobiotic requires endosomal TLR trafficking and signaling from the late endosome and endolysosome but not type I IFN" The Journal of Immunology, vol. 199 / Issue 11, pp. 3739-3747, Dec. 2017.

(Continued)

*Primary Examiner* — Prema M Mertz
(74) *Attorney, Agent, or Firm* — Amster, Rothstein & Ebenstein LLP

(57) ABSTRACT

Exemplary methods, compositions and uses thereof can be provided for preventing, reducing and/or treating loss of muscle function. In particular, e.g., it is possible to administer to a subject a pharmaceutical composition comprising a therapeutically effective amount of an agent that enhances Interleukin-6 (IL) release during exercise, and optionally a pharmaceutically acceptable carrier or excipient.

4 Claims, 8 Drawing Sheets

Specification includes a Sequence Listing.

(56) References Cited

OTHER PUBLICATIONS

Ma Y, et al. "Interleukin-6 gene transfer reverses body weight gain and fatty liver in obese mice" Biochimica et Biophysica Acta—Molecular Basis of Disease, vol. 1852 / Issue 5, pp. 1001-1011, May 2015.
Ferron M, et al. "Intermittent injections of osteocalcin improve glucose metabolism and prevent type 2 diabetes in mice" Bone, vol. 50 / Issue 2, pp. 568-575, Feb. 2012.
Johanson et al., 1995, J. Biol. Chem. 270:9459-9471.
Johnston & Power, 1999, Virol. 73:2491-2498; Poeschla et al., 1998, Nat. Med. 4:354-357.
Kaplitt et al., 1994, Nature Genetics, 8:148-154.
Karlin et al., 1993, Proc. Natl. Acad. Sci. USA 90:5873-5877.
Kim et al., 1998, J. Virol. 72:811-816.
Kreuter et al., 2003, Pharm. Res. 20:409-416.
Lebkowski et al., 1988, Mol. Cell. Biol. 8:3988-3996.
Laface et al., 1998, Virology, 162:483-486.
Lu et al., 2006, Cancer Res. 66:11878-11887.
McLaughlin et al., 1988, J. Virol., 62:1963-1973.
Naldini et al., 1996, Science 272:263-267.
Needleman et al., 1970, J. Mol. Biol. 48:444-453.
Ohi et al., 1990, Gene, 89:279-282.
Novakovic ZM, et al. "Oral delivery of mouse [d-Leu-4]-OB3, a synthetic peptide amide with leptinlike activity, in male C57BL/6J wild-type and ob/ob mice: effects on energy balance, glycaemic control and serum osteocalcin levels" Diabetes, Obesity, and Metabolism, vol. 12 / Issue 6, pp. 532-539, Jun. 2010.
Zhou B, et al. "Osteocalcin reverses endoplasmic reticulum stress and improves impaired insulin sensitivity secondary to diet-induced obesity through nuclear factor-$_K$B signaling pathway" Endocrinology, vol. 154 / Issue 3, pp. 1055-1068, Mar. 2013.
Pardridge, 2007, Pharm. Res. 24:1733-1744.
Poeschla et al., 1996, Proc. Natl. Acad. Sci. USA 93:11395-11399.
Poser & Price, 1979, J. Biol. Chem. 254:431-436.
Poser et al., 1980, J. Biol. Chem. 255:8685-8691.
Li YP,n et al. "Proinflammatory cytokines tumor necrosis factor-alpha and IL-6, but not IL-1, down-regulate the osteocalcin gene promoter" The Journal of Immunology, vol. 148 / Issue 3, pp. 788-794, Feb. 1992.
Rattan et al., 1992, Ann. New York Acad. Sci. 663:48-62.
Retro-vectors for Human Gene Therapy, ed. C. P. Hodgson, Springer Verlag, 1996.
Russell & Miller, 1996, J. Virol. 70:217-222.
Samulski et al., 1989, J. Virol., 63:3822-3828.
Schumacher et al., 1996, Science 271:1854-1857.
Seifter et al., 1990, Meth. Enzymol. 182:626-646.
Sequence Analysis in Molecular Biology, van Heinje, G., Academic Press, 1987.
Sequence Analysis Primer, Gribskov, M. and Devereux, J., eds., M Stockton Press, New York, 1991.
Simon et al., 1992, Proc. Natl. Acad. Sci. 89:9367-9371.
Srinivasakumar et al., 1997, J. Virol. 71:5841-5848.
Taylor et al., 1990, J. Clin. Endocrin. Metab. 70:467-472.
The Development of Human Gene Therapy, Theodore Friedmann, Ed., Cold Spring Harbor Laboratory Press, Cold Spring Harbor, N.Y., 1999.
Tratschin et al., 1984, Mol. Cell. Biol., 4:2072-2081.
Walsh et al., 1992, Proc. Natl. Acad. Sci. USA 89:7257-7261.
Walsh et al., 1994, Blood 84:1492-1500.
Wu et al., 1999, J. Virol. 73:4498-4501.
Zhou et al., 1994, J. Exp. Med., 179:1867-1875.
Zufferey et al., 1997, Nat. Biotechnol. 15:871-875.
Garnero et al., 1994, J. Bone Miner. Res. 9:255-264 (abstract only).
International Search Report and Written Opinion for International Patent Application No. PCT/US2020/027942 mailed on Aug. 16, 2021.
Mera, Paula, et al. "Osteocalcin is necessary and sufficient to maintain muscle mass in older mice." Molecular metabolism 5.10 (Jul. 16, 2016): 1042-1047.
Mera, Paula, et al. "Osteocalcin signaling in myofibers is necessary and sufficient for optimum adaptation to exercise." Cell metabolism 23.6 (Jun. 14, 2016): 1078-1092.

* cited by examiner

Myocyte specific *Il6* knockout

Osteoblast specific *Il6* receptor knockout

Hepatocyte specific *Gprc6a* knockout

METHODS, COMPOSITIONS AND USES THEREOF FOR REVERSING SARCOPENIA

CROSS REFERENCE TO RELATED APPLICATIONS

This application is a continuation of International Patent Application No. PCT/US2021/027942 filed on Apr. 19, 2021, which relates to and claims priority from U.S. Provisional Patent Application Ser. No. 63/011,956, filed Apr. 17, 2020, the entire disclosures of which are incorporated herein by reference.

STATEMENT OF GOVERNMENT INTEREST

This invention was made with Government support under Grant No. AR073180 awarded by the National Institutes of Health. The government has certain rights in the invention.

FIELD OF THE DISCLOSURE

The present disclosure is directed to methods, compositions and uses thereof for preventing and treating loss of muscle function and/or loss of muscle mass in a patient suffering from or at risk for suffering from sarcopenia. For example, the patient may have declined exercise capacity associated with hip fracture, cancer, liver cirrhosis, Cushing's disease, mitochondrial diseases, kidney failure, diabetes and/or aging.

BACKGROUND INFORMATION

Osteocalcin, one of the very few osteoblast-specific proteins, has several features of a hormone. For instance, it is synthesized as a pre-pro-molecule and is secreted in the general circulation (Hauschka et al., 1989, Physiol. Review 69:990-1047; Price, 1989, Connect. Tissue Res. 21:51-57 (discussion 57-60)). Because of their exquisite cell-specific expression, the osteocalcin genes have been intensively studied to identify osteoblast-specific transcription factors and to define the molecular bases of bone physiology (Ducy et al., 2000, Science 289:1501-1504; Harada & Rodan, 2003, Nature 423:349-355).

Osteocalcin is the most abundant non-collagenous protein found associated with the mineralized bone matrix and it is currently being used as a biological marker for clinical assessment of bone turnover. Osteocalcin is a small (46-50 amino acid residues) bone specific protein that contains 3 gamma-carboxylated glutamic acid residues in its primary structure. The name osteocalcin (osteo, Greek for bone; calc, Latin for lime salts; in, protein) derives from the protein's ability to bind $Ca^{2+}$ and its abundance in bone. Osteocalcin undergoes a peculiar post-translational modification whereby glutamic acid residues are carboxylated to form gamma-carboxyglutamic acid (Gla) residues; hence osteocalcin's other name, bone Gla protein (Hauschka et al., 1989, Physiol. Review 69:990-1047).

Mature human osteocalcin contains 49 amino acids with a predicted molecular mass of 5,800 kDa (Poser et al., 1980, J. Biol. Chem. 255:8685-8691). Mature human osteocalcin has the following exemplary amino acid sequence: YLYQWLGAPV PYPDPLEPRR EVCELNPDCD ELADHIGFQE AYRRFYGPV (SEQ ID NO: 32).

Osteocalcin is synthesized primarily by osteoblasts and ondontoblasts and comprises 15 to 20% of the non-collagenous protein of bone. Poser et al., 1980, J. Biol. Chem. 255:8685-8691 showed that mature osteocalcin contains three carboxyglutamic acid residues which are formed by post-translational vitamin K-dependent modification of glutamic acid residues. The carboxylated Gla residues are at positions 17, 21 and 24 of mature human osteocalcin. Some human osteocalcin has been shown to contain only 2 Gla residues (Poser & Price, 1979, J. Biol. Chem. 254:431-436).

Osteocalcin has several features of a hormone. Ducy et al., 1996, Nature 382:448-452 demonstrated that mineralized bone from aging osteocalcin-deficient mice was two times thicker than that of wild-type. It was shown that the absence of osteocalcin led to an increase in bone formation without impairing bone resorption and did not affect mineralization. Multiple immunoreactive forms of human osteocalcin have been discovered in circulation (Garnero et al., 1994, J. Bone Miner. Res. 9:255-264) and also in urine (Taylor et al., 1990, J. Clin. Endocrin. Metab. 70:467-472). Fragments of human osteocalcin can be produced either during osteoclastic degradation of bone matrix or as the result of the catabolic breakdown of the circulating protein after synthesis by osteoblasts.

Accordingly, there may be a need to address and/or at least partially overcome at least some of the prior deficiencies described herein.

SUMMARY OF EXEMPLARY EMBODIMENTS

Such issues and/or deficiencies can at least be partially addressed and/or overcome, a method for preventing or treating loss of muscle function can be provided according to certain exemplary embodiments of the present disclosure. Such exemplary method can comprise, e.g., administering to a subject a pharmaceutical composition comprising a therapeutically effective amount of an agent that enhances Interleukin-6 (IL) release or activity, e.g., during exercise, and optionally a pharmaceutically acceptable carrier or excipient. The subject may suffer from sarcopenia. The subject may suffer from at least one condition selected from the group consisting of hip fracture, cancer, liver cirrhosis, Cushing's disease, Duchene's muscular dystrophy, mitochondrial diseases, kidney failure, diabetes and aging. In certain exemplary embodiments, the agent may further prevent or treat loss of muscle mass.

The exemplary agent can be an endogenous osteocalcin peptide or an engineered osteocalcin peptide. The engineered osteocalcin can be an osteocalcin with a C-terminal truncation, an osteocalcin with an N-terminal stabilizing mutation that eliminates cleavage by inactivating protease, and/or a molecule comprising osteocalcin and an Ig Fc region fused to an N-terminus of the osteocalcin.

The exemplary agent can be an IL6-Bisphosphonate fusion peptide. In certain exemplary embodiments, the agent may be a Gprc6a agonist.

According to certain exemplary embodiments of the present disclosure, it is possible to utilize an agent that enhances Interleukin-6 (IL) release or activity for preventing or treating loss of muscle function. In other exemplary embodiments of the present disclosure, it is possible to use an agent that enhances Interleukin-6 (IL) release or activity in manufacturing a medicament for preventing or treating loss of muscle function.

These and other objects, features and advantages of the exemplary embodiments of the present disclosure will become apparent upon reading the following detailed description of the exemplary embodiments of the present disclosure, when taken in conjunction with the appended claims.

BRIEF DESCRIPTION OF DRAWINGS

Further objects, features and advantages of the present disclosure will become apparent from the following detailed description taken in conjunction with the accompanying Figures showing illustrative embodiments of the present disclosure, in which.

Figure 1:
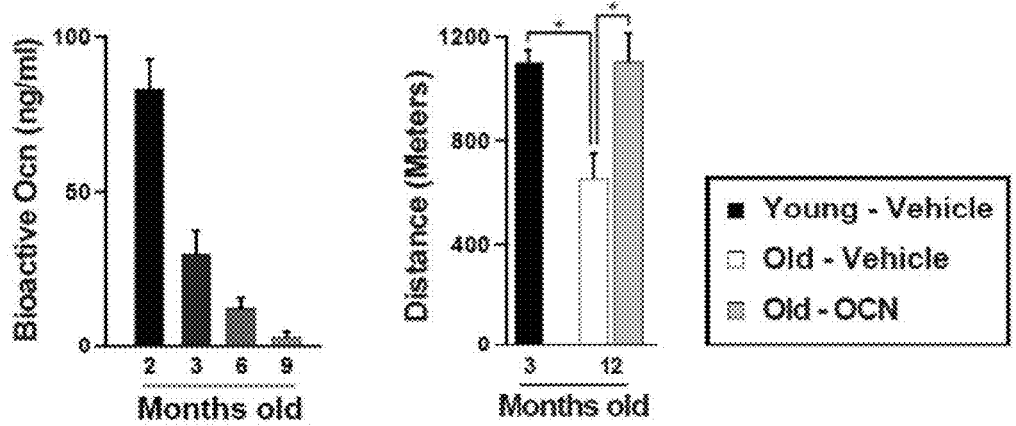
FIG. 1 is a set of exemplary graphs illustrating that osteocalcin (OCN) corrects the age-related decline in exercise.

Throughout the drawings, the same reference numerals and characters, unless otherwise stated, are used to denote like features, elements, components or portions of the illustrated embodiments. Moreover, while the present disclosure will now be described in detail with reference to the figures, it is done so in connection with the illustrative embodiments and is not limited by the certain exemplary embodiments illustrated in the figures and the appended claims.

DETAILED DESCRIPTION OF EXEMPLARY EMBODIMENTS

Sarcopenia is a muscle disease characterized by the coexistence of two of the following three manifestations: loss of muscle mass, loss of grip strength and/or loss of exercise capacity. Multiple diseases and conditions of varied origin may cause sarcopenia. For example, sarcopenia may develop post hip fracture, in cancer, liver cirrhosis, Cushing's disease, mitochondrial diseases, kidney failure, diabetes and aging. There is no approved drug to treat any form of sarcopenia. Multiple drugs have been developed to target muscle mass only (Table 1).

TABLE 1

| Class | Company | Drug | Muscle mass | Exercise capacity |
|---|---|---|---|---|
| Myostatin inhibitor | Novartis | BYM338 | ✓ | ~~~ |
| | Eli Lilly | LY2495655 | ✓ | ~~~ |
| | Regeneron | REGN1033 | ✓ | ~~~ |
| | Pfizer | PF-06252616 | ✓ | ~~~ |
| | Biogen | BIIB110 | ✓ | ~~~ |
| Ghrelin analogue | Helsinn | Anamorelin | ✓ | ~~~ |
| | Oxeia | SUN11031 | ✓ | ~~~ |
| Testosterone analogue | Merck/GTx | Enbosarm | ✓ | ~~~ |
| | GSK | GSK2849466 | ✓ | ~~~ |
| | Viking | VK5211 | ✓ | ~~~ |

Common diseases that can have defects in exercise capacity include and are not limited to, e.g., sarcopenia, hip fracture, liver cirrhosis, hypercortisolism (Cushing's or iatrogenic), cancer cachexia, cachexia in COPD, and rehabilitation from ICU induced loss in muscle mass and function.

Other diseases that can have defects in exercise capacity include and are not limited to, e.g., Duchene's muscular dystrophy, Becker's muscular dystrophy, SMA (as an complement after ASO/GTx to increase 6MWT), Amyotrophic lateral sclerosis (ALS), Facioscapulohumeral muscular dystrophy, Primary mitochondrial myopathies (PMM) (an umbrella category), Fatty acid oxidation disorder (FAOD), Friedreich's ataxia, Charcot-Tooth-Marie disease type 2K, Hereditary spastic paraplegia 7, inclusion body myositis, polymyositis, inclusion body myositis, dermatomyositis, Wilson's disease, Barth syndrome, GRACILE syndrome, Kearns-Sayre syndrome, Leigh syndrome, Maternally inherited deafness and diabetes (MIDD), Mitochondrial DNA depletion syndrome, Mitochondrial encephalomyopathy lactic acidosis, and stroke-like (MELAS), Mitochondrial Neurogastrointestinal encephalomyopathy (MNGIE), Mitochondrial recessive ataxia syndrome (MIRAS), Myoclonus epilepsy with ragged red fibers (MERFF), Neuropathy, ataxia, and retinitis pigmentosa (NARP), and Pearson syndrome.

It has been determined, according to certain exemplary embodiments of the present disclosure that Osteocalcin, a bone-derived hormone, can up-regulate myofiber energetics. It was also further examined whether an osteocalcin treatment might preserve muscle function and/or muscle mass in a clinically relevant mouse model of sarcopenia. To address this question, in exemplary embodiments of the present disclosure, it has been recapitulated the sarcopenia present in iatrogenic Cushing's disease using a one-month chronic infusion of dexamethasone that reduced running capacity by 50% and diminished gastrocnemius muscle mass by 30%. Previous classes of drugs developed to treat sarcopenia, such as SARMs, ghrelin analogues and myostatin inhibitors, have succeeded in increasing muscle mass but have failed to improve muscle function. In contrast, treatment with osteocalcin fully rescued the running capacity of dexamethasone-treated mice. This effect was specific to certain organ systems, as osteocalcin had no effect on the high blood pressure also present in this disease model. Corticosteroids are most commonly used to treat autoimmune diseases and, accordingly, circulating lymphocyte counts were decreased by 50% after dexamethasone treatment. Treatment with osteocalcin did not interfere with nor did it exacerbate dexamethasone-induced immune suppression. While osteocalcin entirely restored running capacity, it improved muscle mass, only in oxidative muscles, i.e., the ones most mobilized during exercise. This suggested that may be a partial uncoupling of muscle function from muscle mass in this model of sarcopenia. To determine if this is the case, mice have been treated with dexamethasone along with either osteocalcin or VK5211, a selective androgen receptor modulator (SARM) in late stage clinical development to increase muscle mass in sarcopenia. Unlike osteocalcin, VK5211 fully restored muscle mass to normal levels inn all types of muscle, i.e., oxidative, glycolytic and mixed muscles, but only had a modest effect on the running capacity in dexamethasone-treated mice. Thus, osteocalcin has been identified as a potential therapeutic target to improve muscle function in iatrogenic Cushing's as well as other sarcopenic states where muscle function is, in part, divorced from muscle mass.

In another recognized model of sarcopenia, the efficacy of osteocalcin has been tested. Specifically, dexamethasone delivered by pumps (69 mg/day) for 28 days has been used in mice. Another group of mice received Dexamethasone plus osteocalcin also delivered by pumps. It was observed that Dexamethasone decreased muscle mass of the mice and their ability to run on a treadmill. The mice receiving Dexamethasone plus osteocalcin had lost significantly less muscle mass than the Dexamethasone alone group. While other compounds resulted in attenuated loss of muscle mass in Dexamethasone mice, the other compounds did not prevent loss of exercise capacity. The dexamethasone plus osteocalcin treated mice had normal exercise capacity.

Further, according to certain exemplary embodiments of the present disclosure, it was determined in vivo evidence that shows that the deleterious effect on muscle function of dexamethasone is presented by a concomitant treatment with osteocalcin in 1 year-old mice. According to certain exemplary embodiments of the present disclosure, it was further determined that when osteocalcin was administered in mice that had already received dexamethasone for two weeks, it could partially revert the deleterious effect of dexamethasone on muscle function.

An exemplary method for preventing or treating loss of muscle function can be provided, according to certain exemplary embodiments of the present disclosure. The exemplary method can comprise administering to a subject a pharmaceutical composition comprising a therapeutically effective amount of an agent that enhances Interleukin-6 (IL) release or activity, e.g., during exercise, and optionally a pharmaceutically acceptable carrier or excipient. The subject may suffer from sarcopenia. The subject may suffer from at least one condition selected from the group consisting of hip fracture, cancer, liver cirrhosis, Cushing's disease, mitochondrial diseases, kidney failure, diabetes and aging.

The subject may suffer from sarcopenia. The subject may suffer from at least one condition selected from the group consisting of hip fracture, cancer, liver cirrhosis, Cushing's disease, Duchene's muscular dystrophy, mitochondrial diseases, kidney failure, diabetes and aging.

In some exemplary embodiments of the present disclosure, the subject may suffer from hip fracture. There are 300,000 cases of hip fracture per year in the U.S. Hip fracture typically involves a 12 month high cost-of-care recovery period. Over 50% of patients never regain mobility/exercise capacity.

According to particular exemplary embodiments of the present disclosure, the subject may suffer from Duchene's muscular dystrophy. Duchene's muscular dystrophy is an orphan disease. There are about 6K patients in the U.S. In other exemplary embodiments, the subject may suffer from Cushing's Disease. Cushing's Disease is an orphan disease. There are about 20,000 patients suffer from Cushing's Disease in the United States.

The agent that enhances Interleukin-6 (IL-6) release or activity used in certain exemplary embodiments of the present disclosure may be selected from the group consisting of a small molecule, a peptide, a protein, or a nucleic acid. In certain exemplary embodiments, the agent is osteocalcin. In other embodiments, the agent is not osteocalcin.

As used in this disclosure, "Osteocalcin" includes, but not limited to, the mature protein and further includes biologically active fragments derived from full-length osteocalcin, or the mature protein, including various domains, as well as variants and engineered osteocalcin as described herein. Human full-length osteocalcin has the amino acid sequence of SEQ ID NO:33 (MRALTLLALL ALAALCIAGQ AGAKPSGAES SKGAAFVSKQ EGSEVVKRPR RYLYQWLGAP VPYPDPLEPR REVCELNPDC DELADHIGFQ EAYRRFYGPV). Human osteocalcin cDNA has the nucleotide sequence of SEQ ID NO:34 (cgcagccacc gagacaccat gagagccctc acactcctcg ccctattggc cctggccgca ctttgcatcg ctggccaggc aggtgcgaag cccagcggtg cagagtccag caaaggtgca gcctttgtgt ccaagcagga gggcagcgag gtagtgaaga gacccaggcg ctacctgtat caatggctgg gagccccagt cccctacccg gatccctgg agcccaggag ggaggtgtgt gagctcaatc cggactgtga cgagttggct gaccacatcg gctttcagga ggcctatcgg cgcttctacg gcccggtcta gggtgtcgct ctgctggcct ggccggcaac cccagttctg ctcctctcca ggcacccttc tttcctcttc cccttgccct tgccctgacc tcccagccct atggatgtgg ggtccccatc atcccagctg ctcccaaata aactccagaa gaggaatctg aaaaaaaaaa aaaaaaaa).

In certain exemplary embodiments, an agent that enhances Interleukin-6 (IL-6) release or activity that is not osteocalcin is used in combination with osteocalcin, e.g., undercarboxylated or uncarboxylated human osteocalcin.

In yet other exemplary embodiments of the present disclosure, the agent may be an IL6 (interleukin-6)-bisphosphonate fusion peptide. The IL6-bisphosphonate fusion peptide may target a pathway upstream of OCN release from the bone and may be a powerful focal regulator of exercise capacity. The IL6-bisphosphonate fusion peptide may be administered to the subject by bimonthly injection, leading to physiological release of OCN. By targeting to bone, off-target effects may be eliminated.

According to still other exemplary embodiments of the present disclosure, the agent may be a Gpr6a agonist. Gprc6a is a promising target for small molecule targeting. Large scale screen of small molecule/structure guided design may be performed using methods known in the art. The Gpr6a agonist may be administered orally to the subject.

Further, an exemplary method for preventing or treating loss of muscle function according to additional exemplary embodiments of the present disclosure. The exemplary method can comprise administering to a subject a pharmaceutical composition comprising a therapeutically effective amount of a form of osteocalcin and optionally a pharmaceutically acceptable carrier or excipient.

In certain exemplary versions of the methods according to exemplary embodiments of the present disclosure, the diseases, disorders and/or conditions in the exemplary embodiments listed herein can be alleviated by administering to the patient a pharmaceutical composition comprising a form of osteocalcin, e.g., undercarboxylated/uncarboxylated osteocalcin, or undercarboxylated/uncarboxylated human osteocalcin. In certain exemplary embodiments, the osteocalcin is human osteocalcin. In certain exemplary embodiments, the osteocalcin is completely uncarboxylated human osteocalcin.

In certain exemplary embodiments of the present disclosure where the agent is undercarboxylated/uncarboxylated osteocalcin, at least one of the glutamic acids in the undercarboxylated/uncarboxylated osteocalcin at the positions corresponding to positions 17, 21 and 24 of mature human osteocalcin is not carboxylated. In certain exemplary embodiments, all three of the glutamic acids in the undercarboxylated/uncarboxylated osteocalcin at the positions corresponding to positions 17, 21 and 24 of mature human osteocalcin are not carboxylated.

In certain exemplary embodiments of the present disclosure, the undercarboxylated/uncarboxylated osteocalcin is a preparation of undercarboxylated/uncarboxylated osteocalcin in which more than about 20% of the total Glu residues at the positions corresponding to positions 17, 21 and 24 of mature human osteocalcin in the preparation are not carboxylated. In certain exemplary embodiments, the undercarboxylated/uncarboxylated osteocalcin shares at least 80% amino acid sequence identity with mature human osteocalcin when the undercarboxylated/uncarboxylated osteocalcin and mature human osteocalcin are aligned for maximum sequence homology. In certain exemplary embodiments, the undercarboxylated/uncarboxylated osteocalcin shares at least about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, or about 98% amino acid sequence identity with mature human osteocalcin when the undercarboxylated/uncarboxylated osteocalcin and mature human osteocalcin are aligned for maximum sequence homology. In certain exemplary embodiments, the undercarboxylated/uncarboxylated osteocalcin differs at 1, 2, 3, 4, 5, 6, 7, 8, 9, or 10 amino acid residues from mature human osteocalcin.

In certain exemplary embodiments of the present disclosure, at least one of the glutamic acids in the undercarboxylated/uncarboxylated osteocalcin at the positions corresponding to positions 17, 21 and 24 of mature human osteocalcin is not carboxylated. In certain exemplary embodiments, all three of the glutamic acids in the undercarboxylated/uncarboxylated osteocalcin at the positions corresponding to positions 17, 21 and 24 of mature human osteocalcin are not carboxylated.

In certain exemplary embodiments, the undercarboxylated/uncarboxylated osteocalcin is a polypeptide selected from the group consisting of:
(a) a fragment comprising mature human osteocalcin missing the last 10 amino acids from the C-terminal end;
(b) a fragment comprising mature human osteocalcin missing the first 10 amino acids from the N-terminal end;
(c) a fragment comprising amino acids 62-90 of SEQ ID NO:33;
(d) a fragment comprising amino acids 1-36 of mature human osteocalcin;
(e) a fragment comprising amino acids 13-26 of mature human osteocalcin; and/or
(f) a fragment comprising amino acids 13-46 of mature human osteocalcin; and
(g) variants of the above.

When positions in two amino acid sequences correspond, it is meant that the two positions align with each other when the two amino acid sequences are aligned with one another to provide maximum homology between them. This same concept of correspondence also applies to nucleic acids.

For example, in the two amino acid sequences AGLYSTVLMGRPS and GLVSTVLMGN, positions 2-11 of the first sequence correspond to positions 1-10 of the second sequence, respectively. Thus, position 2 of the first sequence corresponds to position 1 of the second sequence; position 4 of the first sequence corresponds to position 3 of the second sequence; etc. It should be noted that a position in one sequence may correspond to a position in another sequence, even if the positions in the two sequences are not occupied by the same amino acid.

According to certain exemplary embodiments of the present disclosure, the pharmaceutical composition comprises a small molecule selected from the group consisting of warfarin, vitamin K inhibitors, and biologically active fragments or variants thereof. In a certain exemplary embodiment, the small molecule is warfarin. In another certain exemplary embodiment, the agent is a small molecule that increases the activity or expression of osteocalcin.

In certain exemplary embodiments of the present disclosure, the pharmaceutical composition comprises about 0.5 mg to about 5 g, about 1 mg to about 1 g, about 5 mg to about 750 mg, about 10 mg to about 500 mg, about 20 mg to about 250 mg, or about 25 mg to about 200 mg, of the agent. In certain exemplary embodiments, the pharmaceutical composition comprises an agent that is formulated into a controlled release preparation. In certain exemplary embodiments, the pharmaceutical composition comprises an agent that is chemically modified to prolong its half-life in the human body.

According to certain exemplary embodiments, the pharmaceutical composition according to the present disclosure comprises an undercarboxylated/uncarboxylated osteocalcin polypeptide comprising an amino acid sequence

YLYQWLGAPVPYPDPLX$_1$PRRX$_2$VCX$_3$LNPDCDEL-ADHIGFQEAYRRFYGP V (SEQ ID NO:38)

wherein X$_1$, X$_2$ and X$_3$ are each independently selected from an amino acid or amino acid analog, with the proviso that if X$_1$, X$_2$ and X$_3$ are each glutamic acid, then X$_1$ is not carboxylated, or less than 50 percent of X$_2$ is carboxylated, and/or less than 50 percent of X$_3$ is carboxylated, or said osteocalcin polypeptide comprises an amino acid sequence that is different from SEQ. ID. NO: 38 at 1 to 7 positions other than X$_1$, X$_2$ and X$_3$; and/or wherein said amino acid sequence can include one or more amide backbone substitutions.

In certain exemplary embodiments of the present disclosure, the osteocalcin polypeptide of SEQ. ID. NO: 38 is a fusion protein. According to certain exemplary embodiments of the present disclosure, the arginine at position 43 of SEQ. ID. NO: 38 is replaced with an amino acid or amino acid analog that reduces susceptibility of the osteocalcin polypeptide to proteolytic degradation. In certain exemplary embodiments, the arginine at position 44 of SEQ. ID. NO: 38 is replaced with β-dimethyl-arginine. In certain exemplary embodiments of the present disclosure, the osteocalcin polypeptide is a retroenantiomer of uncarboxylated human osteocalcin (1-49).

Various exemplary embodiments of the present disclosure facilitate the use of an agent that enhances Interleukin-6 (IL) release or activity, e.g., an undercarboxylated/uncarboxylated osteocalcin polypeptide, or mimetic, variants or derivatives thereof, for the manufacture of a medicament for prevention, reduction and/or treatment of loss of muscle function in humans.

The form of osteocalcin (OCN) may be an endogenous OCN peptide, an endogenous human OCN peptide or an engineered OCN peptide (e.g., an engineered human OCN peptide). The endogenous OCN peptide may be administered to the subject by daily subcutaneous injection.

The endogenous OCN is safe with no recorded negative side-effects in animal models.

The engineered osteocalcin may be administered to the patient, for example, weekly or bimonthly via subcutaneous injection. The engineered osteocalcin may show improved efficacy over endogenous OCN. Examples of the engineered osteocalcin include an osteocalcin with a C-terminal truncation, an osteocalcin with an N-terminal stabilizing mutation that eliminates cleavage by inactivating protease, and a molecule comprising osteocalcin and an Ig Fc region fused to an N-terminus of the osteocalcin.

The engineered human osteocalcin may be a C terminal post CPE peptide that comprises or consists of an amino acid sequence of YLYQWLGAPVPYPDPLEPR-REVCELNPDCDELADHIGFQEAY (SEQ ID NO: 1). The engineered human osteocalcin may comprise or consists of an amino acid sequence that shares at least about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, or about 98% amino acid sequence identity with the amino acid sequence of SEQ ID NO: 1. The engineered osteocalcin may be a C terminal di-arginine peptide that comprises or consists of an amino acid sequence of YLYQWLGAPVPYPDPLEPRREVCELNPDCDELA-DHIGFQEAYRR (SEQ ID NO: 2). The engineered human osteocalcin may comprise or consists of an amino acid sequence that shares at least about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, or about 98% amino acid sequence identity with the amino acid sequence of SEQ ID NO: 2. The osteocalcin with a C-terminal truncation may have increased potency at Gprc6a (OCN receptor) and/or improved efficacy in exercise capacity.

The exemplary engineered human osteocalcin with an N-terminal stabilizing mutation may comprises a single amino acid substitution at an N-terminal location of OCN. The mutation may eliminate cleavage by inactivating protease, thereby increasing half-life and resulting in longer dosing interval (e.g., one or more week).

The exemplary engineered human osteocalcin with an N-terminal mutation may comprise or consists of an amino acid sequence of YLYQWLAAPVPYPDPLEPR-REVCELNPDCDELADHIGFQEAYRRFYGPV (SEQ ID NO: 3), YLYQWLGAAVPYPDPLEPR-REVCELNPDCDELADHIGFQEAYRRFYGPV (SEQ ID NO: 4), YLYQWLGAPAPYPDPLEPR-REVCELNPDCDELADHIGFQEAYRRFYGPV (SEQ ID NO: 5), YLYQWLGAPVAYPDPLEPR-REVCELNPDCDELADHIGFQEAYRRFYGPV (SEQ ID NO: 6), YLYQWLGAPVPAPDPLEPR-REVCELNPDCDELADHIGFQEAYRRFYGPV (SEQ ID NO: 7), YLYQWLGAPVPYADPLEPR-REVCELNPDCDELADHIGFQEAYRRFYGPV (SEQ ID NO: 8), YLYQWLGAPVPYPAPLEPR-REVCELNPDCDELADHIGFQEAYRRFYGPV (SEQ ID NO: 9), YLYQWLGAPVPYPDALEPR-REVCELNPDCDELADHIGFQEAYRRFYGPV (SEQ ID NO: 10), or YLYQWLGAPVPYPDPAEPR-REVCELNPDCDELADHIGFQEAYRRFYGPV (SEQ ID NO: 11). The engineered human osteocalcin may comprise or consists of an amino acid sequence that shares at least about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, or about 98% amino acid sequence identity with any of the amino acid sequences of SEQ ID NO: 3 to SEQ ID NO: 11.

The engineered human osteocalcin with an N-terminal mutation may comprise or consists of an amino acid sequence of YLYQWLAAPVPYPDPLEPR-REVCELNPDCDELADHIGFQEAYRR (SEQ ID NO: 12), YLYQWLGAAVPYPDPLEPRREVCELNPDCDELA-DHIGFQEAYRR (SEQ ID NO: 13), YLYQWLGAPAPY-PDPLEPRREVCELNPDCDELADHIGFQEAYRR (SEQ ID NO: 14), YLYQWLGAPVAYPDPLEPR-REVCELNPDCDELADHIGFQEAYRR (SEQ ID NO: 15), YLYQWLGAPVPAPDPLEPRREVCELNPDCDELA-DHIGFQEAYRR (SEQ ID NO: 16), YLYQWLGAPVPY-ADPLEPRREVCELNPDCDELADHIGFQEAYRR (SEQ ID NO: 17), YLYQWLGAPVPYPAPLEPR-REVCELNPDCDELADHIGFQEAYRR (SEQ ID NO: 18), YLYQWLGAPVPYPDALEPRREVCELNPDCDELA-DHIGFQEAYRR (SEQ ID NO: 19), or YLYQWL-GAPVPYPDPAEPRREVCELNPDCDELA-DHIGFQEAYRR (SEQ ID NO: 20). The exemplary engineered human osteocalcin may comprise or consists of an amino acid sequence that shares at least about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, or about 98% amino acid sequence identity with any of the amino acid sequences of SEQ ID NO: 12 to SEQ ID NO: 20.

The exemplary engineered human osteocalcin with an N-terminal mutation may comprise or consists of an amino acid sequence of YLYQWLAAPVPYPDPLEPR-REVCELNPDCDELADHIGFQEAY (SEQ ID NO: 21), YLYQWLGAAVPYPDPLEPRREVCELNPDCDELA-DHIGFQEAY (SEQ ID NO: 22), YLYQWLGAPAPY-PDPLEPRREVCELNPDCDELADHIGFQEAY (SEQ ID NO: 23), YLYQWLGAPVAYPDPLEPR-REVCELNPDCDELADHIGFQEAY (SEQ ID NO: 24), YLYQWLGAPVPAPDPLEPRREVCELNPDCDELA-DHIGFQEAY (SEQ ID NO: 25), YLYQWLGAPVPY-ADPLEPRREVCELNPDCDELADHIGFQEAY (SEQ ID NO: 26), YLYQWLGAPVPYPAPLEPR-REVCELNPDCDELADHIGFQEAY (SEQ ID NO: 27), YLYQWLGAPVPYPDALEPRREVCELNPDCDELA-DHIGFQEAY (SEQ ID NO: 28), or YLYQWL-GAPVPYPDPAEPRREVCELNPDCDELADHIGFQEAY (SEQ ID NO: 29). The engineered human osteocalcin may comprise or consists of an amino acid sequence that shares at least about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, or about 98% amino acid sequence identity with any of the amino acid sequences of SEQ ID NO: 21 to SEQ ID NO: 29.

The exemplary molecule can comprise osteocalcin and an Ig Fc region fused to an N-terminus of the osteocalcin may have increased half-life and longer dosing interval (e.g., one or more week). The exemplary molecule can comprise human osteocalcin and a human Ig Fc region fused to an N-terminus of the human osteocalcin may comprise or consists of an amino acid sequence of EPKSCDKTH-TCPPCPAPEAAGGPSVFLFPPKPKDTLMISRTPE- VTCVVVCVSHEDPEV KFNVVYVDGVEVHNAKTKPREEQYNSTYRVVSVLTVLHQDWLNGKEYKCKVSNKA LPAPIEKTISKAKGQPREPQVYTLPPSRDELTKNQVSLTCLVKGFYPSDIAVEWESNG QPENNYKTTPPVLDSDGSFFLYSKLTVDKSRWQQGNVFSCSVMHEALHNHYTQKSL SLSPGKYLYQWLGAPVPYPDPLEPRREVCELNPDCDELADHIGFQEAYRRFYGPV (SEQ ID NO: 30). The engineered human osteocalcin may comprise or consists of an amino acid sequence that shares at least about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, or about 98% amino acid sequence identity with the amino acid sequence of SEQ ID NO: 30.

The exemplary molecule can comprise human osteocalcin and a human Ig Fc region fused to an C-terminus of the human osteocalcin may comprise or consists of an amino acid sequence of YLYQWLGAPVPYPDPLEPRREVCELNPDCDELADHIGFQEAYRRFYGPVEPKSCDKT HTCPPCPAPEAAGGPSVFLFPPKPKDTLMISRTPEVTCVVVCVSHEDPEVKFNWYVD GVEVHNAKTKPREEQYNSTYRVVSVLTVLHQDWLNGKEYKCKVSNKALPAPIEKTI SKAKGQPREPQVYTLPPSRDELTKNQVSLTCLVKGFYPSDIAVEWESNGQPENNYKT TPPVLDSDGSFFLYSKLTVDKSRWQQGNVFSCSVMHEALHNHYTQKSLSLSPGK (SEQ ID NO: 31). The exemplary engineered human osteocalcin may comprise or consists of an amino acid sequence that shares at least about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, or about 98% amino acid sequence identity with the amino acid sequence of SEQ ID NO: 31.

According to an aspect of the present disclosure, provided is a method of preventing or treating loss of muscle function comprising administering to a subject a pharmaceutical composition comprising a therapeutically effective amount of an agent that enhances Liver Factor 1 release or activity and optionally a pharmaceutically acceptable carrier or excipient. The subject may suffer from sarcopenia. Symptoms of sarcopenia may include a progressive loss of muscle mass and/or muscle functions. It is a nearly universal hallmark of aging and often occurs after bone mass decreases. It cellular and molecular underpinnings are unknown.

The subject may suffer from at least one condition selected from the group consisting of hip fracture, cancer, liver cirrhosis, Cushing's disease, Duchene's muscular dystrophy, mitochondrial diseases, kidney failure, diabetes and aging. In certain exemplary embodiments, the agent may further prevent or treat loss of muscle mass.

A "subject" may be a mammal, preferably a human, but can also be a companion animal such as dogs or cats, or farm animals such as horses, cattle, pigs, or sheep. In certain exemplary embodiments, the subject is a patient who is at least 55 years of age. In some exemplary embodiments of the present disclosure, the patient is at least 60, 65, 70, 75, or 80 years old. In certain exemplary embodiments of the present disclosure, the patient is a human who is between 55 and 80 years old, between 60 and 75 years old, or between 65 and 70 years old. In certain exemplary embodiments, the patient is a human who is between 55 and 60 years old, between 65 and 70 years old, between 70 and 75 years old, between 75 and 80 years old, between 80 and 85 years old, or between 85 and 90 years old.

A patient in need of prevention, reduction and/or treatment according to methods of the present disclosure includes a patient known to have, or suspected of having, or is at risk of developing loss of muscle function, e.g., loss of skeletal muscle function. Such a patient in need of treatment could be, e.g., a mammal known to have low undercarboxylated/uncarboxylated osteocalcin levels. Patients in need of treatment by the methods of the present disclosure include patients who are known to be in need of therapy to increase serum undercarboxylated/uncarboxylated levels in order to treat loss of muscle function.

In certain exemplary embodiments of the present disclosure, a patient in need of prevention, reduction and/or treatment of loss of muscle function by the methods of the present disclosure may also not include a patient being administered the therapeutic agents described herein only for a purpose other than to treat loss of muscle function. Thus, e.g., a patient in need of prevention, reduction and/or treatment of loss of muscle function by the methods of the present disclosure does not include a patient being treated with osteocalcin only for the purpose of alleviating a bone mass disease, or a metabolic disorder such as metabolic syndrome, glucose intolerance, type 1 diabetes, type 2 diabetes, atherosclerosis, or obesity. Nor does it include a patient being treated with osteocalcin only for the purpose of causing an increase in glucose tolerance, an increase in insulin production, an increase insulin sensitivity, an increase in pancreatic beta-cell proliferation, an increase in adiponectin serum level, a reduction of oxidized phospholipids, a regression of atherosclerotic plaques, a decrease in inflammatory protein biosynthesis, a reduction in plasma cholesterol, a reduction in vascular smooth muscle cell (VSMC) proliferation and number, or a decrease in the thickness of arterial plaque.

A patient in need of prevention, reduction and/or treatment of loss of muscle function by or using the exemplary embodiments of the methods according to the present disclosure may also not include a patient being treated with osteocalcin only for the purpose of alleviating a male reproductive disorder or a cognitive disorder.

According to certain exemplary embodiments of the present disclosure, a patient in need of prevention, reduction, and/or treatment of loss of muscle function by the methods of the present disclosure may also not include a patient being treated with osteocalcin that is not undercarboxylated/uncarboxylated osteocalcin, e.g., fully carboxylated osteocalcin.

Exemplary data showing that osteocalcin signaling in myofibers favors adaptation to exercise because it increases uptake and utilization of glucose into the tricarboxylic acid cycle and promotes fatty acids utilization are included in International Patent Application Publication WO 2016/081728, the disclosure of which is incorporated herein by reference. Osteocalcin signaling in myofibers is also the main determinant of the exercise-induced upregulation of Interleukin-6, a myokine that favors the generation of bioactive osteocalcin and of nutrients made available for myofibers. Furthermore, circulating osteocalcin levels decline steeply before mid-life and increase less during exercise in older than in younger mice. This explains why exogenous osteocalcin increases exercise capacity in young mice and confers to 15 months-old mice exercise capacity of 3 month-old mice. Thus, there is an osteocalcin-interleukin- 6 axis that can be necessary to enhance muscle function during exercise and can be harnessed to reverse age-induced decline in exercise capacity.

Exemplary data showing that, by signaling in myofibers, osteocalcin favors adaptation to exercise because it promotes glucose uptake and utilization in the tricarboxylic acid (TCA) cycle as well as utilization of FAs are also included in International Patent Application Publication WO 2016/081728, the disclosure of which is incorporated herein by reference. Osteocalcin signaling in myofibers is also responsible for most of the increase during exercise of the circulating levels of interleukin-6 (IL-6) a myokine that favors glucose and FA production, and signals in osteoblasts to favor the production of bioactive osteocalcin. In contrast, circulating osteocalcin levels decrease sharply before mid-life in all species tested, and do not increase during exercise in older mice to the same extent than in young mice. In agreement with the functions of osteocalcin and with the evolution of its circulating levels over time, exogenous osteocalcin increases the exercise capacity of young mice and confers to 12 to 15 month-old mice the exercise capacity of 3 month-old mice. These results reveal the existence of a crosstalk between osteocalcin signaling in myofibers and IL-6 that, along with the ability of IL-6 to generate glucose and FAs, promotes adaptation to exercise and can be harnessed to increase the exercise capacity of young mice and normalize that of older ones.

Other exemplary aspects according to exemplary embodiments of the present disclosure are directed to diagnostic methods based on detection of the level of undercarboxylated/uncarboxylated osteocalcin in a patient, which level is associated with disorders related to loss of muscle function and/or loss of muscle mass in mammals.

In one exemplary aspect, the method of diagnosing loss of muscle function and/or loss of muscle mass in a patient according to exemplary embodiments of the present disclosure can comprise (i) determining a patient level of undercarboxylated/uncarboxylated osteocalcin in a biological sample taken from the patient, (ii) comparing the patient level of undercarboxylated/uncarboxylated osteocalcin and a control level of undercarboxylated/uncarboxylated osteocalcin, and (iii) if the patient level is significantly lower than the control level, then diagnosing the patient as having, or being at risk for, loss of muscle function and/or loss of muscle mass. A further exemplary step and/or procedure can then be to inform the patient or the patient's healthcare provider of the diagnosis.

Other exemplary aspects of the exemplary embodiments of the present disclosure are directed to diagnostic methods based on detection of decreased ratios of undercarboxylated/uncarboxylated versus carboxylated osteocalcin. Such ratios may be associated with loss of muscle function and/or loss of muscle mass in mammals. In one exemplary aspect, the method of diagnosing a disorder related to loss of muscle function and/or loss of muscle mass in a patient according to the exemplary embodiments of the present disclosure can comprise (i) determining a patient ratio of undercarboxylated/uncarboxylated vs. carboxylated osteocalcin in a biological sample taken from the patient, (ii) comparing the patient ratio of undercarboxylated/uncarboxylated vs carboxylated osteocalcin and a control ratio of undercarboxylated/uncarboxylated vs carboxylated osteocalcin, and (iii) if the patient ratio is significantly lower than the control ratio, then the patient is diagnosed has having, or being at risk for, loss of muscle function and/or loss of muscle mass. A further exemplary step and/or procedure can then be to inform the patient or the patient's healthcare provider of the diagnosis.

Pharmaceutical Compositions For Use In Exemplary Methods

The exemplary embodiments of the present disclosure provide pharmaceutical compositions for use in the prevention, reduction and/or treatment of loss of muscle function and/or loss of muscle mass in mammals comprising an agent that enhances Interleukin-6 (IL) release or activity. The agent may be selected from the group consisting of small molecules, polypeptides, proteins and nucleic acids. The pharmaceutical compositions of the present disclosure provide an amount of the agent effective to prevent, reduce or treat loss of muscle function and/or loss of muscle mass in mammals.

According to certain exemplary embodiments of the present disclosure, the pharmaceutical compositions can comprise an agent that enhances Interleukin-6 (IL) release or activity are administered together with another therapeutic agent. In some exemplary embodiments, the agent that enhances Interleukin-6 release or activity and the other therapeutic agent can be present in the same pharmaceutical composition. In other exemplary embodiments, the agent that enhances Interleukin-6 release or activity and the other therapeutic agent can be administered in separate pharmaceutical compositions.

According to further exemplary embodiments of the present disclosure, the agent that enhances Interleukin-6 release or activity can be the only active pharmaceutical ingredient present in the pharmaceutical compositions.

Biologically active fragments or variants of the therapeutic agents are also within the scope of the present disclosure. By "biologically active" is meant capable of enhancing Interleukin-6 release or activity.

"Biologically active" also refers to fragments or variants of osteocalcin that retain the ability of enhancing Interleukin-6 release or activity to prevent, reduce or treat sarcopenia or loss of muscle function in mammals.

In certain exemplary embodiments, the compositions for use in the methods of the present disclosure may comprise one or more of the endogenous or engineered human osteocalcin fragments described herein.

The primary sequence of osteocalcin is highly conserved among species and it is one of the ten most abundant proteins in the human body, suggesting that its function is preserved throughout evolution among bony vertebrates. Conserved features include 3 Gla residues at positions 17, 21, and 24 and a disulfide bridge between Cys23 and Cys29. In addition, most species contain a hydroxyproline at position 9. The N-terminus of osteocalcin shows highest sequence variation in comparison to other parts of the molecule. The high degree of conservation of human and mouse osteocalcin underscores the relevance of the mouse as an animal model for the human, in both healthy and diseased states, and validates the therapeutic and diagnostic use of osteocalcin to treat loss of muscle function in humans based on the experimental data derived from the mouse model disclosed herein.

The exemplary embodiments of the present disclosure can also provide or facilitate the use of endogenous or engineered polypeptide fragments of osteocalcin. Fragments can be derived from the full-length, naturally occurring amino acid sequence of osteocalcin (e.g., SEQ. ID. NO:33). Fragments may also be derived from mature osteocalcin (e.g., SEQ. ID. NO:32). The present disclosure also encompasses fragments of the variants of osteocalcin described herein. A fragment can comprise an amino acid sequence of any length that is biologically active.

One exemplary particular fragment is a fragment can comprise positions 1-36 of mature human osteocalcin. Another particular exemplary fragment can be a fragment comprising positions 20-49 of mature human osteocalcin. Other exemplary fragments can be designed to contain Pro13 to Tyr76 or Pro13 to Asn26 of mature human osteocalcin. Additionally, exemplary fragments can be provided containing the cysteine residues at positions 23 and 29 of mature human osteocalcin, and capable of forming a disulfide bond between those two cysteines, are useful.

Exemplary fragments can be discrete (not fused to other amino acids or polypeptides) or can be within a larger polypeptide. Further, several exemplary fragments can be comprised within a single larger polypeptide. In one embodiment, a fragment designed for expression in a host can have heterologous pre- and pro-polypeptide regions fused to the amino terminus of the osteocalcin fragment and/or an additional region fused to the carboxyl terminus of the exemplary fragment.

The exemplary embodiments of the present disclosure can be provided for use in the compositions and methods of the present disclosure are variants of osteocalcin and the engineered osteocalcin fragments described above. "Variants" refers to osteocalcin peptides that contain modifications in their amino acid sequences such as one or more amino acid substitutions, additions, deletions and/or insertions but that are still biologically active. In some examples, the antigenic and/or immunogenic properties of the variants are not substantially altered, relative to the corresponding peptide from which the variant was derived. Such modifications may be readily introduced using standard mutagenesis techniques, such as oligonucleotide directed site-specific mutagenesis as taught, for example, by Adelman et al., 1983, DNA 2:183, or by chemical synthesis. Exemplary variants and fragments are not mutually exclusive terms. Fragments can also include peptides that may contain one or more amino acid substitutions, additions, deletions and/or insertions such that the fragments are still biologically active.

One exemplary particular type of variant that is within the scope of the present disclosure is a variant in which one of more of the positions corresponding to positions 17, 21, and 24 of mature human osteocalcin is occupied by an amino acid that is not glutamic acid. In certain exemplary embodiments, the amino acid that is not glutamic acid is also not aspartic acid. Such exemplary variants can be versions of undercarboxylated osteocalcin because at least one of the three positions corresponding to positions 17, 21, and 24 of mature human osteocalcin is not carboxylated glutamic acid, since at least one of those positions is not occupied by glutamic acid.

In other exemplary embodiments, the osteocalcin variants comprise an amino acid sequence that includes one or more amide backbone substitutions.

Fully functional variants typically contain only conservative variation or variation in non-critical residues or in non-critical regions. Functional variants can also contain substitutions of similar amino acids, which results in no change, or an insignificant change, in function. Alternatively, such substitutions may positively or negatively affect function to some degree. The activity of such functional osteocalcin variants can be determined using assays such as those described herein.

Exemplary variants can be naturally occurring or can be made by recombinant means, or chemical synthesis, to provide useful and novel characteristics for undercarboxylated/uncarboxylated osteocalcin. For example, the variant osteocalcin polypeptides may have reduced immunogenicity, increased serum half-life, increased bioavailability, and/or increased potency. In certain exemplary embodiments, serum half-life is increased by substituting one or more of the native Arg residues at positions 19, 20, 43, and 44 of mature osteocalcin with another amino acid or an amino acid analog, e.g., β-dimethyl-arginine. Such substitutions can be combined with the other changes in the native amino acid sequence of osteocalcin described herein.

The exemplary embodiments of the present disclosure can be provided for use in the pharmaceutical compositions and methods of the present disclosure are variants that are also derivatives of the osteocalcin and osteocalcin fragments described above. Derivatization is a technique used in chemistry which transforms a chemical compound into a product of similar chemical structure, called derivative. Generally, a specific functional group of the compound participates in the derivatization reaction and transforms the compound to a derivate of different reactivity, solubility, boiling point, melting point, aggregate state, functional activity, or chemical composition. Resulting new chemical properties can be used for quantification or separation of the derivatized compound or can be used to optimize the derivatized compound as a therapeutic agent. The well-known techniques for derivatization can be applied to the above-described osteocalcin and osteocalcin fragments. Thus, derivatives of the osteocalcin and osteocalcin fragments described above will contain amino acids that have been chemically modified in some way so that they differ from the natural amino acids.

Provided also are osteocalcin mimetics. "Mimetic" refers to a synthetic chemical compound that has substantially the same structural and functional characteristics of a naturally or non-naturally occurring osteocalcin polypeptide, and includes, for instance, polypeptide- and polynucleotide-like polymers having modified backbones, side chains, and/or bases. Peptide mimetics are commonly used in the pharmaceutical industry as non-peptide drugs with properties analogous to those of the template peptide. Generally, mimetics are structurally similar (i.e., have the same shape) to a paradigm polypeptide that has a biological or pharmacological activity, but one or more polypeptide linkages are replaced. The mimetic can be either entirely composed of synthetic, non-natural analogues of amino acids or is a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or activity.

By way of examples that can be adapted to osteocalcin by those skilled in the art, Cho et al., 1993, Science 261:1303-1305 discloses an "unnatural biopolymer" consisting of chiral aminocarbonate monomers substituted with a variety of side chains, synthesis of a library of such polymers, and screening for binding affinity to a monoclonal antibody. Simon et al., 1992, Proc. Natl. Acad. Sci. 89:9367-9371 discloses a polymer consisting of N-substituted glycines ("peptoids") with diverse side chains. Schumacher et al, 1996, Science 271:1854-1857 discloses D-peptide ligands identified by screening phage libraries of L-peptides against proteins synthesized with D-amino acids and then synthesizing a selected L-peptide using D-amino acids. Brody et al., 1999, Mol. Diagn. 4:381-8 describes generation and screening of hundreds to thousands of aptamers.

A particular type of osteocalcin variant within the scope of the exemplary embodiments of the present disclosure can be an osteocalcin mimetic in which one or more backbone amides is replaced by a different chemical structure or in which one or more amino acids are replaced by an amino acid analog. In a certain exemplary embodiment, the osteocalcin mimetic is a retroenantiomer of uncarboxylated human osteocalcin.

Osteocalcin, as well as its fragments and variants, is optionally produced by chemical synthesis or recombinant methods and may be produced as a modified osteocalcin molecule (i.e., osteocalcin fragments or variants) as described herein. Osteocalcin polypeptides and/or osteocalcin variants can be produced by any conventional means (Houghten, 1985, Proc. Natl. Acad. Sci. USA 82:5131-5135). Simultaneous multiple peptide synthesis is described in U.S. Pat. No. 4,631,211 and can also be used. When produced recombinantly, osteocalcin may be produced as a fusion protein, e.g., a GST-osteocalcin fusion protein.

Undercarboxylated/uncarboxylated osteocalcin molecules that can be used in the methods according to the exemplary embodiments of the present disclosure include proteins substantially homologous to human osteocalcin, including proteins derived from another organism, i.e., an ortholog of human osteocalcin. One particular ortholog is mouse osteocalcin. Mouse osteocalcin gene 1 cDNA is SEQ ID NO:35 (agaacagaca agtcccacac agcagcttgg cccagaccta gcagacacca tgaggaccat ctttctgctc actctgctga ccctggctgc gctctgtctc tctgacctca cagatgccaa gcccagcgagc cctgagtctg acaaagcctt catgtccaag caggagggca ataaggtagt gaacagactc cggcgctacc ttggagcctc agtcccagc ccagatcccc tggagcccac ccgggagcag tgtgagctta accctgcttg tgacgagcta tcagaccagt atggcttgaa gaccgcctac aaacgcatct atggtatcac tatttaggac ctgtgctgcc ctaaagccaa actctggcag ctcggctttg gctgctctcc gggacttgat cctccctgtc ctctctctct gccctgcaag tatggatgtc acagcagctc caaaataaag ttcagatgag gaagtgcaaa aaaaaaaaaa aaaa); mouse osteocalcin gene 2 cDNA is SEQ ID NO:36 (gaacagacaa gtcccacaca gcagcttggt gcacacctag cagacaccat gaggaccctc tctctgctca ctctgctggc cctggctgcg ctctgtctct ctgacctcac agatcccaag cccagcggcc ctgagtctga caaagccttc atgtccaagc aggagggcaa taaggtagtg aacagactcc ggcgctacct tggagcctca gtccccagcc cagatccct ggagcccacc cgggagcagt gtgagcttaa ccctgcttgt gacgagctat cagaccagta tggcttgaag accgcctaca aacgcatcta cggtatcact atttaggacc tgtgctgccc taaagccaaa ctctggcagc tcggctttgg ctgctctccg ggacttgatc ctccctgtcc tctctctctg ccctgcaagt atggatgtca cagcagctcc aaaataaagt tcagatgagg); the amino acid sequence of mouse osteocalcin gene 1 and gene 2 is SEQ ID NO:37 (MRTLSLLTLL ALAALCLSDL TDPKPSGPES DKAFMSKQEG NKVVNRLRRY LGASVPSPDP LEPTREQCEL NPACDELSDQ YGLKTAYKRI YGITI).

As used herein, two proteins can be substantially homologous when their amino acid sequences are at least about 70% homologous. Typically, the degree of homology is at least about 75%, about 80%, about 85%, and most typically at least about 90%, about 95%, about 97%, about 98% or about 99% or more. "Homology" between two amino acid sequences or nucleic acid sequences can be determined by using the algorithms disclosed herein. These algorithms can also be used to determine percent identity between two amino acid sequences or nucleic acid sequences. Homologous sequences include those sequences that are substantially identical.

To determine the percent homology or percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). Preferably, the length of a reference sequence aligned for comparison purposes is at least 30%, preferably at least 40%, more preferably at least 50%, even more preferably at least 60%, and even more preferably at least 70%, 80%, or 90% or more of the length of the sequence that the reference sequence is compared to. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences.

The exemplary embodiments of the present disclosure can also encompass polypeptides having a lower degree of identity but which have sufficient similarity so as to perform one or more of the same functions performed by osteocalcin. Similarity is determined by considering conserved amino acid substitutions. Such substitutions are those that substitute a given amino acid in a polypeptide by another amino acid of like characteristics. Conservative substitutions are likely to be phenotypically silent. Guidance concerning which amino acid changes are likely to be phenotypically silent may be found in Bowie et al., 1990, Science 247:1306-1310.

Examples of conservative substitutions are the replacements, one for another, among the hydrophobic amino acids Ala, Val, Leu, and Ile; interchange of the hydroxyl residues Ser and Thr; exchange of the acidic residues Asp and Glu; substitution between the amide residues Asn and Gln; exchange of the basic residues Lys, His and Arg; replacements among the aromatic residues Phe, Trp and Tyr; exchange of the polar residues Gln and Asn; and exchange of the small residues Ala, Ser, Thr, Met, and Gly.

The comparison of sequences and determination of percent identity and homology between two osteocalcin polypeptides can be accomplished using a mathematical algorithm. See, for example, Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H G., eds., Humana Press, New Jersey, 1994; Sequence Analysis in Molecular Biology, van Heinje, G., Academic Press, 1987; and Sequence Analysis Primer, Gribskov, M. and Devereux, J., eds., M Stockton Press, New York, 1991. A non-limiting example of such a mathematical algorithm is described in Karlin et al., 1993, Proc. Natl. Acad. Sci. USA 90:5873-5877.

The percent identity or homology between two osteocalcin amino acid sequences may be determined using the Needleman et al., 1970, J. Mol. Biol. 48:444-453 algorithm.

A substantially homologous osteocalcin, according to the exemplary embodiments of the present disclosure, can also be a polypeptide encoded by a nucleic acid sequence capable of hybridizing to the human osteocalcin nucleic acid sequence under highly stringent conditions, e.g., hybridization to filter-bound DNA in 0.5 M NaHPO4, 7% sodium dodecyl sulfate (SDS), 1 mM EDTA at 65° C., and washing in 0.1×SSC/0.1% SDS at 68° C. (Ausubel et al., eds., 1989, Current Protocols in Molecular Biology, Vol. I, Green Publishing Associates, Inc., and John Wiley & sons, Inc., New York, at p. 2.10.3) and encoding a functionally equivalent gene product; or under less stringent conditions, such as moderately stringent conditions, e.g., washing in 0.2×SSC/

0.1% SDS at 42° C. (Ausubel et al., 1989 supra), yet which still encodes a biologically active undercarboxylated/uncarboxylated osteocalcin.

A substantially homologous osteocalcin according to the exemplary embodiments of the present disclosure may also be a polypeptide encoded by a nucleic acid sequence capable of hybridizing to a sequence having at least 70-75%, typically at least about 80-85%, and most typically at least about 90-95%, 97%, 98% or 99% identity to the human osteocalcin nucleic acid sequence, under stringent conditions, e.g., hybridization to filter-bound DNA in 0.5 M NaHPO4, 7% sodium dodecyl sulfate (SDS), 1 mM EDTA at 65° C., and washing in 0.1×SSC/0.1% SDS at 68° C. (Ausubel F. M. et al., eds., 1989, Current Protocols in Molecular Biology, Vol. I, Green Publishing Associates, Inc., and John Wiley & sons, Inc., New York, at p. 2.10.3) and encoding a functionally equivalent gene product; or under less stringent conditions, such as moderately stringent conditions, e.g., washing in 0.2×SSC/0.1% SDS at 42° C. (Ausubel et al., 1989 supra), yet which still encodes a biologically active undercarboxylated/uncarboxylated osteocalcin.

It should be understood that a biologically active fragment or variant of human osteocalcin may contain a different number of amino acids than native human osteocalcin. Accordingly, the position number of the amino acid residues corresponding to positions 17, 21, and 24 of mature human osteocalcin may differ in the exemplary fragment or variant. One skilled in the art would easily recognize such corresponding positions from a comparison of the amino acid sequence of the fragment or variant with the amino acid sequence of mature human osteocalcin.

Peptides corresponding to fusion proteins in which full length osteocalcin, mature osteocalcin, or an osteocalcin fragment or an engineered osteocalcin is fused to an unrelated protein or polypeptide are also within the scope of the present disclosure and can be designed on the basis of the osteocalcin nucleotide and amino acid sequences disclosed herein. Such fusion proteins include fusions to an enzyme, fluorescent protein, or luminescent protein which provides a marker function. In a particular exemplary embodiment of the present disclosure, the fusion protein can comprise fusion to a polypeptide capable of targeting the osteocalcin to a particular target cell or location in the body. For example, osteocalcin polypeptide sequences may be fused to a ligand molecule capable of targeting the fusion protein to a cell expressing the receptor for said ligand. In a certain exemplary embodiment, osteocalcin polypeptide sequences may be fused to a ligand capable of targeting the fusion protein to specific neurons in the brain of a mammal.

Osteocalcin can also be made as part of a chimeric protein for drug screening or use in making recombinant protein. These chimeric proteins comprise an osteocalcin peptide sequence linked to a heterologous peptide having an amino acid sequence not substantially homologous to the osteocalcin. The heterologous peptide can be fused to the N-terminus or C-terminus of osteocalcin or can be internally located. In one embodiment, the fusion protein does not affect osteocalcin function. For example, the fusion protein can be a GST-fusion protein in which the osteocalcin sequences are fused to the N- or C-terminus of the GST sequences. Other types of fusion proteins include, but are not limited to, enzymatic fusion proteins, for example beta-galactosidase fusions, yeast two-hybrid GAL-4 fusions, poly-His fusions and Ig fusions. Such fusion proteins, particularly poly-His fusions, can facilitate the purification of recombinant osteocalcin. In certain host cells (e.g., mammalian host cells), expression and/or secretion of a protein can be increased by using a heterologous signal sequence. Therefore, the fusion protein may contain a heterologous signal sequence at its N-terminus.

Those skilled in art would understand how to adapt well-known techniques for use with osteocalcin. For example, European Patent Publication No. 0 464 533 describes fusion proteins comprising various portions of immunoglobulin constant regions (Fc regions). The Fc region is useful in therapy and diagnosis and thus results, for example, in improved pharmacokinetic properties (see, e.g., European Patent Publication No. 0 232 262). In drug discovery, for example, human proteins have been fused with Fc regions for the purpose of high-throughput screening assays to identify antagonists (see, e.g., Bennett et al., 1995, J. Mol. Recog. 8:52-58 and Johanson et al., 1995, J. Biol. Chem. 270:9459-9471). Thus, various embodiments of this disclosure also utilize soluble fusion proteins containing an osteocalcin polypeptide and various portions of the constant regions of heavy or light chains of immunoglobulins of various subclasses (e.g., IgG, IgM, lgA, IgE, 1gB). A particular immunoglobulin is the constant part of the heavy chain of human IgG, particularly IgG1, where fusion takes place at the hinge region. For some uses, it is desirable to remove the Fc region after the fusion protein has been used for its intended purpose. In a certain exemplary embodiment, the Fc part can be removed in a simple way by a cleavage sequence, which is also incorporated and can be cleaved, e.g., with factor Xa.

A chimeric or fusion protein can be produced by standard recombinant DNA techniques. For example, DNA fragments coding for the different protein sequences can be ligated together in-frame in accordance with conventional techniques. In another exemplary embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., 1992, Current Protocols in Molecular Biology). Moreover, many expression vectors are commercially available that already encode a fusion moiety (e.g., a GST protein). An osteocalcin-encoding nucleic acid can be cloned into such an expression vector such that the fusion moiety is linked in-frame to osteocalcin.

Chimeric osteocalcin proteins can be produced in which one or more functional sites are derived from a different isoform, or from another osteocalcin molecule from another species. Sites also could be derived from osteocalcin-related proteins that occur in the mammalian genome but which have not yet been discovered or characterized.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art.

Accordingly, the osteocalcin polypeptides useful in the methods according to the exemplary embodiments of the present disclosure also encompass derivatives which contain a substituted non-naturally occurring amino acid residue that is not one encoded by the genetic code, in which a substituent group is included, in which the mature polypeptide is fused with another compound, such as a compound to increase the half-life of the polypeptide (for example, polyethylene glycol), or in which the additional amino acids are fused to the osteocalcin polypeptide, such as a leader or secretory sequence or a sequence for purification of the osteocalcin polypeptide or a pro-protein sequence.

Undercarboxylated/uncarboxylated osteocalcin can be modified according to known methods in medicinal chemistry to increase its stability, half-life, uptake or efficacy. Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent crosslinks, formation of cystine, formation of pyroglutamate, formylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

In a specific exemplary embodiment of the present disclosure, modifications may be made to the osteocalcin to reduce susceptibility to proteolysis at residue Arg43 as a means for increasing serum half life. Such modifications include, for example, the use of retroenantio isomers, D-amino acids, or other amino acid analogs.

Acylation of the N-terminal amino group can be accomplished using a hydrophilic compound, such as hydroorotic acid or the like, or by reaction with a suitable isocyanate, such as methylisocyanate or isopropylisocyanate, to create a urea moiety at the N-terminus. Other agents can also be N-terminally linked that will increase the duration of action of the osteocalcin derivative.

Reductive amination is the process by which ammonia is condensed with aldehydes or ketones to form imines which are subsequently reduced to amines. Reductive amination is a useful method for conjugating undercarboxylated/uncarboxylated osteocalcin and its fragments or variants to polyethylene glycol (PEG). Covalent linkage of PEG to undercarboxylated/uncarboxylated osteocalcin and its fragments and variants may result in conjugates with increased water solubility, altered bioavailability, pharmacokinetics, immunogenic properties, and biological activities. See, e.g., Bentley et al., 1998, J. Pharm. Sci. 87:1446-1449.

Several particularly common modifications that may be applied to undercarboxylated/uncarboxylated osteocalcin and its fragments and variants such as glycosylation, lipid attachment, sulfation, hydroxylation and ADP-ribosylation are described in most basic texts, such as Proteins-Structure and Molecular Properties, 2nd ed., T. E. Creighton, W. H. Freeman and Company, New York (1993). Many detailed reviews are available on this subject, such as by Wold, F., Posttranslational Covalent Modification of Proteins, B. C. Johnson, Ed., Academic Press, New York 1-12 (1983); Seifter et al., 1990, Meth. Enzymol. 182:626-646 and Rattan et al., 1992, Ann. New York Acad. Sci. 663:48-62.

As is also well known, polypeptides are not always entirely linear. For instance, polypeptides may be branched as a result of ubiquitination, and they may be circular, with or without branching, generally as a result of post-translation events, including natural processing events and events brought about by human manipulation which do not occur naturally. Circular, branched and branched circular polypeptides may be synthesized by non-translational natural processes and by synthetic methods. Well-known techniques for preparing such non-linear polypeptides may be adapted by those skilled in the art to produce non-linear osteocalcin polypeptides.

Modifications can occur anywhere in the undercarboxylated/uncarboxylated osteocalcin and its fragments and variants, including the peptide backbone, the amino acid sidechains and the amino or carboxyl termini. Blockage of the amino or carboxyl group in a polypeptide, or both, by a covalent modification, is common in naturally-occurring and synthetic polypeptides and may be applied to the undercarboxylated/uncarboxylated osteocalcin or its fragments and variants used in the present disclosure. For instance, the amino terminal residue of polypeptides made in *E. coli*, prior to proteolytic processing, almost invariably will be N-formylmethionine. Thus, the use of undercarboxylated/uncarboxylated osteocalcin and its fragments and variants with N-formylmethionine as the amino terminal residue are within the scope of the present disclosure.

A brief description of various protein modifications that come within the scope of the exemplary embodiments of the present disclosure are set forth in the table below:

TABLE 2

| Protein Modification | Description |
| --- | --- |
| Acetylation | Acetylation of N-terminus or ε-lysines. Introducing an acetyl group into a protein, specifically, the substitution of an acetyl group for an active hydrogen atom. A reaction involving the replacement of the hydrogen atom of a hydroxyl group with an acetyl group ($CH_3CO$) yields a specific ester, the acetate. Acetic anhydride is commonly used as an acetylating agent, which reacts with free hydroxyl groups. Acylation may facilitate addition of other functional groups. A common reaction is acylation of e.g., conserved lysine residues with a biotin appendage. |
| ADP-ribosylation | Covalently linking proteins or other compounds via an arginine-specific reaction. |
| Alkylation | Alkylation is the transfer of an alkyl group from one molecule to another. The alkyl group may be transferred as an alkyl carbocation, a free radical or a carbanion (or their equivalents). Alkylation is accomplished by using certain functional groups such as alkyl electrophiles, alkyl nucleophiles or sometimes alkyl radicals or carbene acceptors. A common example is methylation (usually at a lysine or arginine residue). |
| Amidation | Reductive animation of the N-terminus. Methods for amidation of insulin are described in U.S. Pat. No. 4,489,159. |

TABLE 2-continued

| Protein Modification | Description |
|---|---|
| Carbamylation | Nigen et al. describes a method of carbamylating hemoglobin. |
| Citrullination | Citrullination involves the addition of citrulline amino acids to the arginine residues of a protein, which is catalyzed by peptidylarginine deaminase enzymes (PADs). This generally converts a positively charged arginine into a neutral citrulline residue, which may affect the hydrophobicity of the protein (and can lead to unfolding). |
| Condensation of amines with aspartate or glutamate | Such reactions, may be used, e.g., to attach a peptide to other proteins labels. |
| Covalent attachment of flavin | Flavin mononucleotide (FAD) may be covalently attached to serine and/or threonine residues. May be used, e.g., as a light-activated tag. |
| Covalent attachment of heme moiety | A heme moiety is generally a prosthetic group that consists of an iron atom contained in the center of a large heterocyclic organic ring, which is referred to as a porphyrin. The heme moiety may be used, e.g., as a tag for the peptide. |
| Attachment of a nucleotide or nucleotide derivative | May be used as a tag or as a basis for further derivatising a peptide. |
| Cross-linking | Cross-linking is a method of covalently joining two proteins. Cross-linkers contain reactive ends to specific functional groups (primary amines, sulfhydryls, etc.) on proteins or other molecules. Several chemical groups may be targets for reactions in proteins and peptides. For example, Ethylene glycol bis[succinimidylsuccinate, Bis[2-(succinimidooxycarbonyloxy)ethyl]sulfone, and Bis[sulfosuccinimidyl] suberate link amines to amines. |
| Cyclization | For example, cyclization of amino acids to create optimized delivery forms that are resistant to, e.g., aminopeptidases (e.g., formation of pyroglutamate, a cyclized form of glutamic acid). |
| Disulfide bond formation | Disulfide bonds in proteins are formed by thiol-disulfide exchange reactions, particularly between cysteine residues (e.g., formation of cystine). |
| Demethylation | See, e.g., U.S. Pat. No. 4,250,088 (Process for demethylating lignin). |
| Formylation | The addition of a formyl group to, e.g., the N-terminus of a protein. See, e.g., U.S. Pat. Nos. 4,059,589, 4,801,742, and 6,350,902. |
| Glycylation | The covalent linkage of one to more than 40 glycine residues to the tubulin C-terminal tail. |
| Glycosylation | Glycosylation may be used to add saccharides (or polysaccharides) to the hydroxy oxygen atoms of serine and threonine side chains (which is also known as O-linked Glycosylation). Glycosylation may also be used to add saccharides (or polysaccharides) to the amide nitrogen of asparagine side chains (which is also known as N-linked Glycosylation), e.g., via oligosaccharyl transferase. |
| GPI anchor formation | The addition of glycosylphosphatidylinositol to the C-terminus of a protein. GPI anchor formation involves the addition of a hydrophobic phosphatidylinositol group-linked through a carbohydrate containing linker (e.g., glucosamine and mannose linked to phosphoryl ethanolamine residue)-to the C-terminal amino acid of a protein. |
| Hydroxylation | Chemical process that introduces one or more hydroxyl groups (—OH) into a protein (or radical). Hydroxylation reactions are typically catalyzed by hydroxylases. Proline is the principal residue to be hydroxylated in proteins, which occurs at the $C^\gamma$ atom, forming hydroxyproline (Hyp). In some cases, proline may be hydroxylated at its $C^\beta$ atom. Lysine may also be hydroxylated on its $C^\delta$ atom, forming hydroxylysine (Hyl). These three reactions are catalyzed by large, multi-subunit enzymes known as prolyl 4-hydroxylase, prolyl 3-hydroxylase and lysyl 5-hydroxylase, respectively. These reactions require iron (as well as molecular oxygen and α-ketoglutarate) to carry out the oxidation, and use ascorbic acid to return the iron to its reduced state. |
| Iodination | See, e.g., U.S. Pat. No. 6,303,326 for a disclosure of an enzyme that is capable of iodinating proteins. U.S. Pat. No. 4,448,764 discloses, e.g., a reagent that may be used to iodinate proteins. |
| ISGylation | Covalently linking a peptide to the ISG15 (Interferon-Stimulated Gene 15) protein, for, e.g., modulating immune response. |

TABLE 2-continued

| Protein Modification | Description |
|---|---|
| Methylation | Reductive methylation of protein amino acids with formaldehyde and sodium cyanoborohydride has been shown to provide up to 25% yield of N-cyanomethyl (—CH$_2$CN) product. The addition of metal ions, such as Ni$^{2+}$, which complex with free cyanide ions, improves reductive methylation yields by suppressing by-product formation. The N-cyanomethyl group itself, produced in good yield when cyanide ion replaces cyanoborohydride, may have some value as a reversible modifier of amino groups in proteins. (Gidley et al.) Methylation may occur at the arginine and lysine residues of a protein, as well as the N- and C-terminus thereof. |
| Myristoylation | Myristoylation involves the covalent attachment of a myristoyl group (a derivative of myristic acid), via an amide bond, to the alpha-amino group of an N-terminal glycine residue. This addition is catalyzed by the N-myristoyltransferase enzyme. |
| Oxidation | Oxidation of cysteines.<br>Oxidation of N-terminal Serine or Threonine residues (followed by hydrazine or aminooxy condensations).<br>Oxidation of glycosylations (followed by hydrazine or aminooxy condensations). |
| Palmitoylation | Palmitoylation is the attachment of fatty acids, such as palmitic acid, to cysteine residues of proteins. Palmitoylation increases the hydrophobicity of a protein. |
| (Poly)glutamylation | Polyglutamylation occurs at the glutamate residues of a protein. Specifically, the gamma-carboxy group of a glutamate will form a peptide-like bond with the amino group of a free glutamate whose alpha-carboxy group may be extended into a polyglutamate chain. The glutamylation reaction is catalyzed by a glutamylase enzyme (or removed by a deglutamylase enzyme). Polyglutamylation has been carried out at the C-terminus of proteins to add up to about six glutamate residues. Using such a reaction, Tubulin and other proteins can be covalently linked to glutamic acid residues. |
| Phosphopantetheinylation | The addition of a 4'-phosphopantetheinyl group. |
| Phosphorylation | A process for phosphorylation of a protein or peptide by contacting a protein or peptide with phosphoric acid in the presence of a non-aqueous apolar organic solvent and contacting the resultant solution with a dehydrating agent is disclosed e.g., in U.S. Pat. No. 4,534,894. Insulin products are described to be amenable to this process. See, e.g., U.S. Pat. No. 4,534,894. Typically, phosphorylation occurs at the serine, threonine, and tyrosine residues of a protein. |
| Prenylation | Prenylation (or isoprenylation or lipidation) is the addition of hydrophobic molecules to a protein. Protein prenylation involves the transfer of either a farnesyl (linear grouping of three isoprene units) or a geranyl-geranyl moiety to C-terminal cysteine(s) of the target protein. |
| Proteolytic Processing | Processing, e.g., cleavage of a protein at a peptide bond. |
| Selenoylation | The exchange of, e.g., a sulfur atom in the peptide for selenium, using a selenium donor, such as selenophosphate. |
| Sulfation | Processes for sulfating hydroxyl moieties, particularly tertiary amines, are described in, e.g., U.S. Pat. No. 6,452,035. A process for sulphation of a protein or peptide by contacting the protein or peptide with sulphuric acid in the presence of a non-aqueous apolar organic solvent and contacting the resultant solution with a dehydrating agent is disclosed. Insulin products are described to be amenable to this process. See, e.g., U.S. Pat. No. 4,534,894. |
| SUMOylation | Covalently linking a peptide a SUMO (small ubiquitin-related Modifier) protein, for, e.g., stabilizing the peptide. |
| Transglutamination | Covalently linking other protein(s) or chemical groups (e.g., PEG) via a bridge at glutamine residues |
| tRNA-mediated addition of amino acids (e.g., arginylation) | For example, the site-specific modification (insertion) of an amino acid analog into a peptide. |
| Ubiquitination | The small peptide ubiquitin is covalently linked to, e.g., lysine residues of a protein. The ubiquitin-proteasome system can be used to carryout such reaction. See, e.g., U.S. 2007-0059731. |

The exemplary embodiments of the present disclosure also encompassthe use of prodrugs of undercarboxylated/uncarboxylated osteocalcin, engineered osteocalcin, or derivatives or variants thereof that can be produced by esterifying the carboxylic acid functions of the undercarboxylated/uncarboxylated osteocalcin or derivative or variant thereof with a lower alcohol, e.g., methanol, ethanol, propanol, isopropanol, butanol, etc. The use of prodrugs of the undercarboxylated/uncarboxylated osteocalcin or derivative or variant thereof that are not esters is also contemplated. For example, pharmaceutically acceptable carbonates, thiocarbonates, N-acyl derivatives, N-acyloxyalkyl derivatives, quaternary derivatives of tertiary amines, N-Mannich bases, Schiff bases, amino acid conjugates, phosphate esters, metal salts and sulfonate esters of the undercarboxylated/uncarboxylated osteocalcin or derivative or variant thereof are also contemplated. In some exemplary embodiments, the prodrugs will contain a biohydrolyzable moiety (e.g., a biohydrolyzable amide, biohydrolyzable carbamate, biohydrolyzable carbonate, biohydrolyzable ester, biohydrolyzable phosphate, or biohydrolyzable ureide analog). Guidance for the preparation of prodrugs of the undercarboxylated/uncarboxylated osteocalcin or derivative or variant thereof disclosed herein can be found in publications such as Design of Prodrugs, Bundgaard, A. Ed., Elsevier, 1985; Design and Application of Prodrugs, A Textbook of Drug Design and Development, Krosgaard-Larsen and H. Bundgaard, Ed., 1991, Chapter 5, pages 113-191; and Bundgaard, H., Advanced Drug Delivery Review, 1992, 8, pages 1-38.

To practice the methods according to the exemplary embodiments of the present disclosure, it may be desirable to recombinantly express endogenous osteocalcin or engineered osteocalcin variants, e.g., by recombinantly expressing a cDNA sequence encoding osteocalcin. The cDNA sequence and deduced amino acid sequence of human osteocalcin is represented in SEQ ID NO:1 and SEQ ID NO:2. Osteocalcin nucleotide sequences may be isolated using a variety of different methods known to those skilled in the art. For example, a cDNA library constructed using RNA from a tissue known to express osteocalcin can be screened using a labeled osteocalcin probe. Alternatively, a genomic library may be screened to derive nucleic acid molecules encoding osteocalcin. Further, osteocalcin nucleic acid sequences may be derived by performing a polymerase chain reaction (PCR) using two oligonucleotide primers designed on the basis of known osteocalcin nucleotide sequences. The template for the reaction may be cDNA obtained by reverse transcription of mRNA prepared from cell lines or tissue known to express osteocalcin.

While the osteocalcin polypeptides and peptides can be chemically synthesized (e.g., see Creighton, 1983, Proteins: Structures and Molecular Principles, W. H. Freeman & Co., N.Y.), large polypeptides derived from osteocalcin and the full length osteocalcin itself may be advantageously produced by recombinant DNA technology using techniques well known in the art for expressing a nucleic acid. Such methods can be used to construct expression vectors containing the osteocalcin nucleotide sequences and appropriate transcriptional and translational control signals. These methods include, for example, in vitro recombinant DNA techniques, synthetic techniques, and in vivo genetic recombination. See, for example, the techniques described in Ausubel et al., 1989, supra.

A variety of host-expression vector systems may be utilized to express the osteocalcin nucleotide sequences. In a certain exemplary embodiment, the osteocalcin peptide or polypeptide is secreted and may be recovered from the culture media.

Appropriate expression systems can be chosen to ensure that the correct modification, processing and subcellular localization of the osteocalcin protein occurs. To this end, bacterial host cells are useful for expression of osteocalcin, as such cells are unable to carboxylate osteocalcin.

The isolated osteocalcin can be purified from cells that naturally express it, e.g., osteoblasts, or purified from cells that naturally express osteocalcin but have been recombinantly modified to overproduce osteocalcin, or purified from cells that that do not naturally express osteocalcin but have been recombinantly modified to express osteocalcin. In a certain exemplary embodiment, a recombinant cell has been manipulated to activate expression of the endogenous osteocalcin gene. For example, International Patent Publications WO 99/15650 and WO 00/49162 describe a method of expressing endogenous genes termed random activation of gene expression (RAGE), which can be used to activate or increase expression of endogenous osteocalcin. The RAGE methodology involves non-homologous recombination of a regulatory sequence to activate expression of a downstream endogenous gene. Alternatively, International Patent Publications WO 94/12650, WO 95/31560, and WO 96/29411, as well as U.S. Pat. Nos. 5,733,761 and 6,270,985, describe a method of increasing expression of an endogenous gene that involves homologous recombination of a DNA construct that includes a targeting sequence, a regulatory sequence, an exon, and a splice-donor site. Upon homologous recombination, a downstream endogenous gene is expressed. The methods of expressing endogenous genes described in the foregoing patents and patent publications are hereby expressly incorporated by reference herein.

In certain exemplary embodiments of methods of the present disclosure where the therapeutic agent is endogenous osteocalcin, engineered osteocalcin described herein or a derivative or variant thereof, the endogenous osteocalcin, engineered osteocalcin described herein or a derivative or variant thereof is administered to a patient in a dosage range of from about 0.5 µg/kg/day to about 100 mg/kg/day, from about 1 µg/kg/day to about 90 mg/kg/day, from about 5 µg/kg/day to about 85 mg/kg/day, from about 10 µg/kg/day to about 80 mg/kg/day, from about 20 µg/kg/day to about 75 mg/kg/day, from about 50 µg/kg/day to about 70 mg/kg/day, from about 150 µg/kg/day to about 65 mg/kg/day, from about 250 µg/kg/day to about 50 mg/kg/day, from about 500 µg/kg/day to about 50 mg/kg/day, from about 1 mg/kg/day to about 50 mg/kg/day, from about 5 mg/kg/day to about 40 mg/kg/day, from about 10 mg/kg/day to about 35 mg/kg/day, from about 15 mg/kg/day to about 30 mg/kg/day, from about 5 mg/kg/day to about 16 mg/kg/day, or from about 5 mg/kg/day to about 15 mg/kg/day.

In certain exemplary embodiments of methods of the present disclosure where the therapeutic agent is endogenous osteocalcin, engineered osteocalcin described herein or a derivative or variant thereof, the endogenous osteocalcin, engineered osteocalcin described herein or a derivative or variant thereof is administered to a patient in a dosage range of from about 0.5 µg/kg/day to about 100 µg/kg/day, from about 1 µg/kg/day to about 80 µg/kg/day, from about 3 µg/kg/day to about 50 µg/kg/day, or from about 3 µg/kg/day to about 30 µg/kg/day.

In certain exemplary embodiments of methods of the present disclosure where the therapeutic agent is endogenous osteocalcin, engineered osteocalcin described herein or a derivative or variant thereof, the endogenous osteocalcin, engineered osteocalcin described herein or a derivative or variant thereof is administered to a patient in a dosage range of from about 0.5 µg/kg/day to about 100 µg/kg/day, from about 1 µg/kg/day to about 80 µg/kg/day, from about 3 µg/kg/day to about 50 µg/kg/day, or from about 3 µg/kg/day to about 30 ng/kg/day.

The exemplary embodiments of the present disclosure encompass the use of the polypeptides, proteins, nucleic acids, small molecules and other therapeutic agents described herein formulated in pharmaceutical compositions to administer to a subject. The therapeutic agents (also referred to as "active compounds") can be incorporated into pharmaceutical compositions suitable for administration to a subject, e.g., a human. Such compositions typically comprise a therapeutic agent and a pharmaceutically acceptable carrier. Preferably, such compositions are non-pyrogenic when administered to humans.

As used herein the language "pharmaceutically acceptable carrier" is intended to include any and all solvents, binders, diluents, disintegrants, lubricants, dispersion media, coatings, antibacterial and antifungal agents, isotonic and absorption delaying agents, and the like, compatible with pharmaceutical administration. The use of such media and agents for pharmaceutically active substances is well known in the art. As long as any conventional media or agent is compatible with the active compound, such media can be used in the compositions of the present disclosure. Supplementary active compounds or therapeutic agents can also be incorporated into the compositions. A pharmaceutical composition according to the exemplary embodiments of the present disclosure can be formulated to be compatible with its intended route of administration. Examples of routes of administration include parenteral, e.g., intravenous, intradermal, intranasal, subcutaneous, oral, inhalation, transdermal (topical), transmucosal, and rectal administration.

The term "administer" is used in its broadest sense and includes any method of introducing the compositions of the present disclosure into a subject. This includes producing polypeptides or polynucleotides in vivo as by transcription or translation of polynucleotides that have been exogenously introduced into a subject. Thus, polypeptides or nucleic acids produced in the subject from the exogenous compositions are encompassed in the term "administer."

Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylene diamine tetra acetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where the therapeutic agents are water soluble) or dispersions and sterile powders for the extemporaneous preparation of sterile injectable solutions or dispersion. For intravenous administration, suitable carriers include physiological saline, bacteriostatic water, Cremophor EL® (BASF, Parsippany, N.J.) or phosphate buffered saline (PBS). In all cases, the composition must be sterile and should be fluid to the extent that easy syringability exists. It should be stable under the conditions of manufacture and storage and should be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of the ingredients enumerated above, as required, followed by filter sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yield a powder of the active ingredient plus any additional desired ingredient from a previously sterile-filtered solution thereof.

Oral compositions generally include an inert diluent or an edible carrier. They can be enclosed in gelatin capsules or compressed into tablets. Depending on the specific conditions being treated, pharmaceutical compositions of the present disclosure for treatment of loss of muscle function in mammals can be formulated and administered systemically or locally. Techniques for formulation and administration can be found in "Remington: The Science and Practice of Pharmacy" ($20^{th}$ edition, Gennaro (ed.) and Gennaro, Lippincott, Williams & Wilkins, 2000). For oral administration, the agent can be contained in enteric forms to survive the stomach or further coated or mixed to be released in a particular region of the GI tract by known methods. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, PRIMOGEL®, or corn starch; a lubricant such as magnesium stearate or STEROTES®; a glidant such as colloidal silicon dioxide; a sweetening agent such as sucrose or saccharin; or a flavoring agent such as peppermint, methyl salicylate, or orange flavoring.

For administration by inhalation, the compounds may be delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

If appropriate, the compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to particular cells with, e.g., monoclonal antibodies) can also be used as pharmaceutically acceptable carriers. These can be prepared according to methods known to those skilled in the art, for example, as described in U.S. Pat. No. 4,522,811.

It is especially advantageous to formulate oral or parenteral compositions in unit dosage form for ease of administration and uniformity of dosage. "Unit dosage form" as used herein refers to physically discrete units suited as unitary dosages for the subject to be treated; each unit containing a predetermined quantity of active compound calculated to produce the desired therapeutic effect in association with the required pharmaceutical carrier. The specification for the unit dosage forms of this disclosure are dictated by and directly dependent on the unique characteristics of the active compound and the particular therapeutic effect to be achieved, and the limitations inherent in the art of compounding such an active compound for the treatment of individuals.

As discussed herein, the agent may be administered continuously by pump or frequently during the day for extended periods of time. In certain exemplary embodiments, the agent may be administered at a rate of from about 0.3-100 μg/hour, preferably about 1-75 μg/hour, more preferably about 5-50 μg/hour, and even more preferably about 10-30 μg/hour. The agent may be administered at a rate of from about 0.1-100 μg/hr, preferably about 1-75 μg/hr, more preferably about 5-50 μg/hr, and even more preferably about 10-30 μg/hr. It will also be appreciated that the effective dosage of antibody, protein, or polypeptide used for treatment may increase or decrease over the course of a particular treatment. Changes in dosage may result and become apparent from monitoring the level of the active compound in a biological sample, preferably blood or serum.

In an exemplary embodiment of the present disclosure, the agent can be delivered by subcutaneous, long-term, automated drug delivery using an osmotic pump to infuse a desired dose of the agent for a desired time. Insulin pumps are widely available and are used by diabetics to automatically deliver insulin over extended periods of time. Such insulin pumps can be adapted to deliver the agent for use in the methods of the present disclosure. The delivery rate of the agent can be readily adjusted through a large range to accommodate changing requirements of an individual (e.g., basal rates and bolus doses). New pumps permit a periodic dosing manner, i.e., liquid is delivered in periodic discrete doses of a small fixed volume rather than in a continuous flow manner. The overall liquid delivery rate for the device is controlled and adjusted by controlling and adjusting the dosing period. The pump can be coupled with a continuous monitoring device and remote unit, such as a system described in U.S. Pat. No. 6,560,471, entitled "Analyte Monitoring Device and Methods of Use." In such an arrangement, the hand-held remote unit that controls the continuous blood monitoring device could wirelessly communicate with and control both the blood monitoring unit and the fluid delivery device delivering therapeutic agents for use in the methods of the present disclosure.

In certain exemplary embodiments of the present disclosure, routine experimentation may be used to determine the appropriate dosage value for each patient by monitoring the effect of the therapeutic agent on serum active compound levels. The agent can be administered once or multiple times per day. Serum active compound levels can be monitored before and during therapy to determine the appropriate amount of therapeutic agent to administer to raise serum active compound levels or bring serum active compound levels to desired levels over extended periods of time. In a certain exemplary embodiment, a patient is tested to determine if his serum active compound levels are significantly lower than normal levels (about 25% below) before administering treatment with the therapeutic agent. The frequency of administration may vary from a single dose per day to multiple doses per day. Particular routes of administration include oral, intravenous and intraperitoneal, but other forms of administration may be chosen as well.

A "therapeutically effective amount" of a protein or polypeptide, small molecule, antibody, or nucleic acid is an amount that achieves the desired therapeutic result. For example, if a therapeutic agent is administered to treat loss of muscle function in mammals, a therapeutically effective amount is an amount that alleviates one or more symptoms related to muscle wasting or a lung disorder while at the same time alleviating one or more symptoms related to a metabolic disorder, a male reproductive disorder, or a cognitive disorder.

A therapeutically effective amount of protein or polypeptide, small molecule or nucleic acid for use in the present disclosure typically varies and can be an amount sufficient to achieve serum therapeutic agent levels typically of between about 1 nanogram per milliliter and about 10 micrograms per milliliter in the subject, or an amount sufficient to achieve serum therapeutic agent levels of between about 1 nanogram per milliliter and about 7 micrograms per milliliter in the subject. Other particular serum therapeutic agent levels include about 0.1 nanogram per milliliter to about 3 micrograms per milliliter, about 0.5 nanograms per milliliter to about 1 microgram per milliliter, about 1 nanogram per milliliter to about 750 nanograms per milliliter, about 5 nanograms per milliliter to about 500 nanograms per milliliter, and about 5 nanograms per milliliter to about 100 nanograms per milliliter.

The exemplary amount of the exemplary therapeutic agent disclosed herein to be administered to a patient in the methods of the present disclosure can be determined by those skilled in the art through routine methods and may range from about 1 mg/kg/day to about 1,000 mg/kg/day, from about 5 mg/kg/day to about 750 mg/kg/day, from about 10 mg/kg/day to about 500 mg/kg/day, from about 25 mg/kg/day to about 250 mg/kg/day, from about 50 mg/kg/day to about 100 mg/kg/day, or other suitable amounts.

The exemplary amount of the exemplary therapeutic agent disclosed herein to be administered to a patient in the methods of the present disclosure also may range from about 1 µg/kg/day to about 1,000 µg/kg/day, from about 5 µg/kg/day to about 750 µg/kg/day, from about 10 µg/kg/day to about 500 µg/kg/day, from about 25 µg/kg/day to about 250 µg/kg/day, or from about 50 µg/kg/day to about 100 µg/kg/day.

The exemplary amount of the exemplary therapeutic agent disclosed herein to be administered to a patient in the methods of the present disclosure also may range from about 1 µg/kg/day to about 1,000 ng/kg/day, from about 5 ng/kg/day to about 750 ng/kg/day, from about 10 ng/kg/day to about 500 ng/kg/day, from about 25 ng/kg/day to about 250 ng/kg/day, or from about 50 ng/kg/day to about 100 ng/kg/day.

The skilled artisan will appreciate that certain factors may influence the dosage required to effectively treat a subject, including but not limited to the severity of the condition, previous treatments, the general health and/or age of the subject, and other disorders or diseases present.

Treatment of a subject with a therapeutically effective amount of a protein, polypeptide, nucleotide or antibody can include a single treatment or, preferably, can include a series of treatments.

Additionally, exemplary methods for preventing or treating loss of muscle function in a subject according to the exemplary embodiments of the present disclosure can comprise administering to the subject a pharmaceutical composition comprising an agent that modulates the Liver Factor 1 signaling pathway, where the agent increases Liver Factor 1 expression or activity.

Exercise is an evolutionarily conserved survival function. The systemic regulation of exercise remains unknown. Exercise capacity declines in hip fracture, cancer, liver cirrhosis, Cushing's disease, mitochondrial diseases, kidney failure, diabetes, and with aging.

Osteocalcin, a bone-derived hormone, signals in myofibers through Gprc6a.

Osteocalcin levels surge after exercise in mice and humans. Osteocalcin favors nutrient uptake and catabolism. Osteocalcin is required for IL6 release during exercise. Osteocalcin is necessary and sufficient for normal exercise capacity. Cell Metabolism, 2016.

In certain exemplary embodiments of the present disclosure, the pharmaceutical composition can comprise about 0.5 mg to about 5 g, about 1 mg to about 1 g, about 5 mg to about 750 mg, about 10 mg to about 500 mg, about 20 mg to about 250 mg, or about 25 mg to about 200 mg, of the agent. In certain exemplary embodiments of the present disclosure, the pharmaceutical composition can comprise an agent that is formulated into a controlled release preparation. In certain exemplary embodiments of the present disclosure, the pharmaceutical composition can comprise an agent that is chemically modified to prolong its half life in the human body.

It can be understood that the appropriate dose of the agent depends upon a number of factors within the knowledge of the ordinarily skilled physician, veterinarian, or researcher. The dose(s) of the agent will vary, for example, depending upon the identity, size, and condition of the subject or sample being treated, further depending upon the route by which the composition is to be administered, and the effect which the practitioner desires the agent to have. It can be furthermore understood that appropriate doses of the agent depend upon the potency of the agent with respect to the expression or activity to be modulated. In addition, it is understood that the specific dose level for any particular subject will depend upon a variety of factors including the activity of the specific compound employed, the age, body weight, general health, and diet of the subject, the time of administration, the route of administration, the rate of excretion, whether other drugs are being administered to the patient, and the degree of expression or activity to be modulated.

Suitable routes of administration of the pharmaceutical compositions useful in the methods of the present disclosure can include oral, intestinal, parenteral, transmucosal, transdermal, intramuscular, subcutaneous, transdermal, rectal, intramedullary, intrathecal, intravenous, intraventricular, intraatrial, intraortal, intraarterial, or intraperitoneal administration. The pharmaceutical compositions useful in the exemplary methods according to exemplary embodiments of the present disclosure can be administered to the subject by a medical device, such as, but not limited to, catheters, balloons, implantable devices, biodegradable implants, prostheses, grafts, sutures, patches, shunts, or stents. In one certain exemplary embodiment, the agent may be coated on a stent for localized administration to the target area. In this situation a slow release preparation of the active compound, for example, may be employed.

The exemplary compounds according to the exemplary embodiments of the present disclosure can also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations and that may be consulted by those skilled in the art for techniques useful for practicing the present disclosure include, but are not limited to, e.g., U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, the disclosure of each of which is incorporated herein by reference.

While uncarboxylated osteocalcin crosses the blood-brain barrier, certain derivatives, variants, or modified forms of osteocalcin may not. In embodiments of the disclosure utilizing a form of osteocalcin that does not cross the blood-brain barrier, one may take advantage of methods known in the art for transporting substances across the blood-brain barrier. For example, the methods disclosed in U.S. Patent Application Publication No. 2013/0034590 or U.S. Patent Application Publication No. 2013/0034572 may be used. The human insulin or transferrin receptor can be utilized by targeting these receptors with a monoclonal antibody-modified osteocalcin conjugate (see, e.g., Pardridge, 2007, Pharm. Res. 24:1733-1744; Beduneau et al., 2008, J. Control. Release 126:44-49). Surfactant coated poly(butylcyanoacrylate) nanoparticles containing modified osteocalcin may be used (Kreuter et al., 2003, Pharm. Res. 20:409-416). Alternatively, cationic carriers such as cationic albumin conjugated to pegylated nanoparticles containing modified osteocalcin may be used to deliver modified osteocalcin to the brain (see, e.g.,Lu et al., 2006, Cancer Res. 66:11878-11887).

In yet another exemplary aspect of the present disclosure, undercarboxylated/uncarboxylated osteocalcin is administered as a pharmaceutical composition with a pharmaceutically acceptable excipient. Exemplary pharmaceutical compositions for undercarboxylated/uncarboxylated osteocalcin include injections as solutions or injections as injectable self-setting or self-gelling mineral polymer hybrids. Undercarboxylated/uncarboxylated osteocalcin may be administered using a porous crystalline biomimetic bioactive composition of calcium phosphate. See U.S. Pat. Nos. 5,830, 682; 6,514,514; and 6,511,958 and U.S. Patent Application Publications Nos. 2006/0063699; 2006/0052327; 2003/0199615; 2003/0158302; 2004/0157864; 2006/0292670; 2007/0099831 and 2006/0257492, all of which are incorporated herein in their entirety by reference.

Exemplary Method(s) of Treatment

The exemplary embodiments of the present disclosure provide exemplary methods for at least one of preventing, reducing or treating loss of muscle function in mammals through enhancing Interleukin-6 (IL) release or activity. The agent may be selected from the group consisting of small molecules, polypeptides, proteins and nucleic acids.

In certain exemplary embodiments, the exemplary methods comprise identifying a patient in need of treatment of sarcopenia and then applying the methods disclosed herein to the patient. Preferably, the patient is a human.

In another exemplary aspect of the present disclosure, a method is provided for at least one of preventing, reducing or treating loss of muscle function in a subject comprising administering to a mammal in need thereof an agent that enhances Interleukin-6 (IL) release or activity, such as undercarboxylated/uncarboxylated osteocalcin, in a therapeutically effective amount such that the loss of muscle function is treated. Preferably, the subject is a human.

In the exemplary methods described herein, it will be understood that "treating" or "alleviating" a disease or disorder encompasses not only improving the disease or disorder or its symptoms but also retarding the progression of the disease or disorder or ameliorating the deleterious effects of the disease or disorder.

The exemplary embodiments of the present disclosure also encompasses the use of gene therapy for at least one of preventing, reducing or treating loss of muscle function. This can be accomplished by introducing a gene encoding osteocalcin or a biologically active fragment or variant thereof into a vector, and transfecting or infecting cells from a mammal afflicted with loss of muscle function or at a high risk of developing loss of muscle function with the vector, according to various methods known in the art. The cells may be transfected or infected by ex vivo or by in vivo methods.

Exemplary methods of gene therapy known in the art can be adapted for use in the methods of the present disclosure. Adeno-associated virus (AAV) is one of the most promising vectors for gene therapy and may be used in the methods of the present disclosure. Conventional methods of gene transfer and gene therapy are described in, e.g., Gene Therapy: Principles and Applications, ed. T. Blackenstein, Springer Verlag, 1999; Gene Therapy Protocols (Methods in Molecular Medicine), ed. P. D. Robbins, Humana Press, 1997; and Retro-vectors for Human Gene Therapy, ed. C. P. Hodgson, Springer Verlag, 1996. AAV is an attractive vector system for human gene therapy because it is non-pathogenic for humans, it has a high frequency of integration, and it can infect non-dividing cells, thus making it useful for delivery of genes into mammalian cells both in tissue culture and in whole animals. See, e.g., Muzyczka, 1992, Curr. Top. Microbiol. Immunol., 158:97-129. Recent studies have demonstrated AAV to be a potentially useful vector for gene delivery. LaFace et al., 1998, Virology, 162:483-486; Zhou et al., 1993, Exp. Hematol. (NY), 21:928-933; Flotte et al., 1993, Proc. Natl. Acad. Sci. USA 90:10613-10617; and Walsh et al., 1994, Blood 84:1492-1500. Recombinant AAV vectors have been used successfully for in vitro and in vivo transduction of marker genes (Kaplitt et al., 1994, Nature Genetics, 8:148-154; Lebkowski et al., 1988, Mol. Cell. Biol. 8:3988-3996; Samulski et al., 1989, J. Virol., 63:3822-3828; Shelling & Smith, 1994, Gene Therapy 1:165-169; Yoder et al., 1994, Blood, 82:suppl. 1:347A; Zhou et al., 1994, J. Exp. Med., 179:1867-1875; Hermonat & Muzyczka, 1984, Proc. Natl. Acad. Sci. USA., 81:6466-6470; Tratschin et al., 1984, Mol. Cell. Biol., 4:2072-2081; McLaughlin et al., 1988, J. Virol., 62:1963-1973) as well as genes involved in human diseases (Flotte et al., 1992, Am. J. Respir. Cell Mol. Biol. 7:349-356; Luo et al., 1994, Blood, 82:suppl. 1,303A; Ohi et al., 1990, Gene, 89:279-282; Walsh et al., 1992, Proc. Natl. Acad. Sci. USA 89:7257-7261; Wei et al., 1994, Gene Therapy, 1:261-268).

In certain other exemplary embodiments of the present disclosure, the gene of interest (e.g., osteocalcin) can be transferred into a target cell using a retroviral vector. Retroviruses refer to viruses that belong to the Retroviridae family, and include oncoviruses, foamy viruses (Russell & Miller, 1996, J. Virol. 70:217-222; Wu et al., 1999, J. Virol. 73:4498-4501, and lentiviruses (for example, HIV-1 (Naldini et al., 1996, Science 272:263-267; Poeschla et al., 1996, Proc. Natl. Acad. Sci. USA 93:11395-11399; Srinivasakumar et al., 1997, J. Virol. 71:5841-5848; Zufferey et al., 1997, Nat. Biotechnol. 15:871-875; Kim et al., 1998, J. Virol. 72:811-816) and feline immunodeficiency virus (Johnston et al., 1999, J. Virol. 73:4991-5000; Johnston & Power, 1999, Virol. 73:2491-2498; Poeschla et al., 1998, Nat. Med. 4:354-357). The disclosures of these publications may be adapted for use in the methods of the present disclosure. Numerous gene therapy methods that take advantage of retroviral vectors for treating a wide variety of diseases are well-known in the art and can be adapted for use in the methods of the present disclosure (see, e.g., U.S. Pat. Nos. 4,405,712 and 4,650,764; Friedmann, 1989, Science, 244:1275-1281; Mulligan, 1993, Science, 260:926-932; Crystal, 1995, Science 270:404-410, and U.S. Pat. No. 6,899,871, each of which are incorporated herein by reference in their entirety). An increasing number of these methods are currently being applied in human clinical trials (Morgan, 1993, BioPharm, 6:32-35; see also The Development of Human Gene Therapy, Theodore Friedmann, Ed., Cold Spring Harbor Laboratory Press, Cold Spring Harbor, N.Y., 1999. ISBN 0-87969-528-5, which is incorporated herein by reference in its entirety).

Efficacy of the exemplary methods of treatment described herein can be monitored by determining whether the methods ameliorate any of the symptoms of the disease or disorder being treated. Alternatively, it is possible to monitor the level of serum active compound, which levels should increase in response to therapy.

The exemplary embodiments of the present disclosure is illustrated herein by the following examples, which should not be construed as limiting. The contents of all references, pending patent applications and published patents, cited throughout this application are hereby expressly incorporated by reference. Those skilled in the art will understand that these exemplary embodiments of the present disclosure may be embodied in many different forms and should not be construed as limited to the embodiments set forth herein. Rather, these exemplary embodiments are provided so that the present disclosure will fully convey the exemplary embodiment of the present disclosure to those skilled in the art. Various exemplary modifications and other exemplary embodiments of the present disclosure will come to mind in one skilled in the art to which this invention pertains having the benefit of the teachings presented in the foregoing description. Although specific terms are employed, they are used as in the art unless otherwise indicated.

EXAMPLES

Example 1

Figure 2:
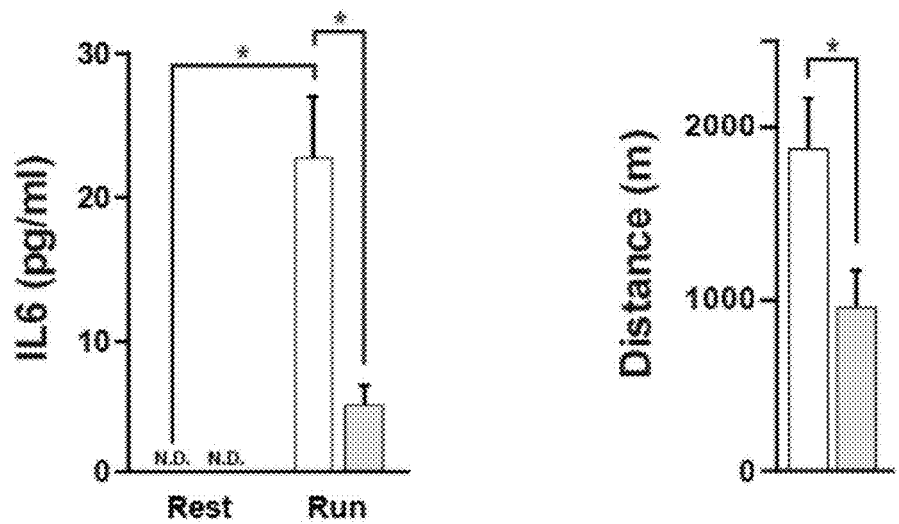
FIG. 2 is a set of exemplary graphs illustrating that muscle-derived IL-6 is beneficial for an endurance exercise.
Figure 3:
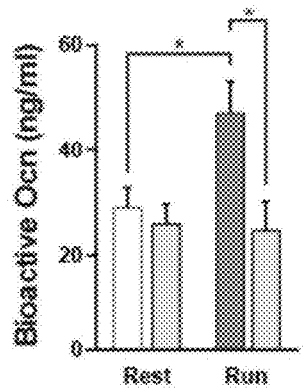
FIG. 3 is a set of exemplary graphs illustrating that muscle-derived IL-6 is beneficial for the endurance exercise by up-regulating osteocalcin (OCN) secretion.
Figure 3:
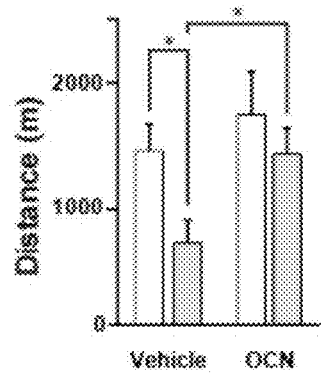
Figure 4:
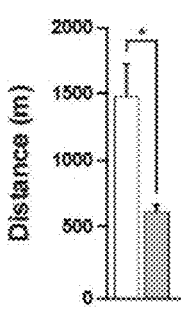
FIGS. 4 and 5 are exemplary graphs illustrating that IL-6 siimaling in bone determines exercise capacity in mice and in human.
Figure 4:
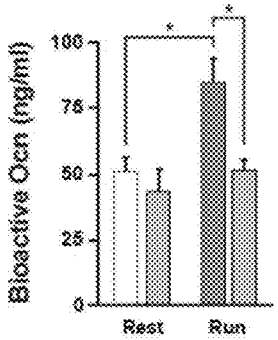
Figure 4:
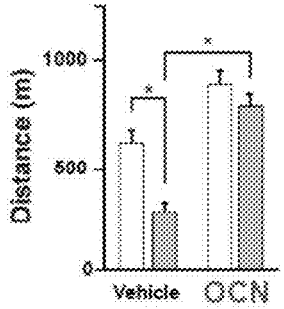
Figure 5:
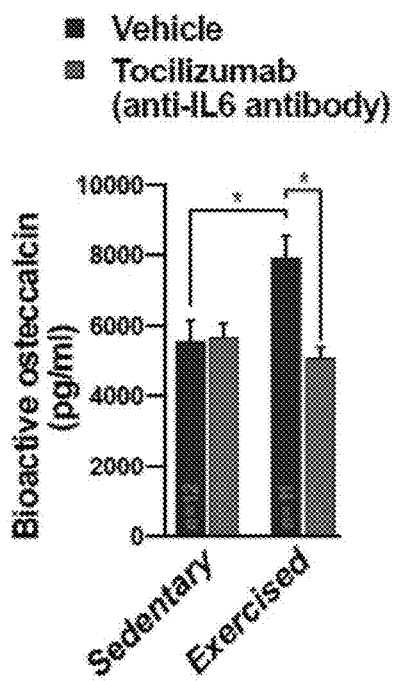

OCN corrects the age-related decline in exercise (see FIG. 1). Muscle-derived IL-6 is needed for endurance exercise (FIG. 2) by up-regulating osteocalcin (OCN) secretion (see FIG. 3). IL-6 signaling in bone determines exercise capacity in mice and in human (FIGS. 4 and 5). Therefore, a feed forward loop between bone and muscle determines exercise capacity in mice and humans.

Example 2

Figure 6:
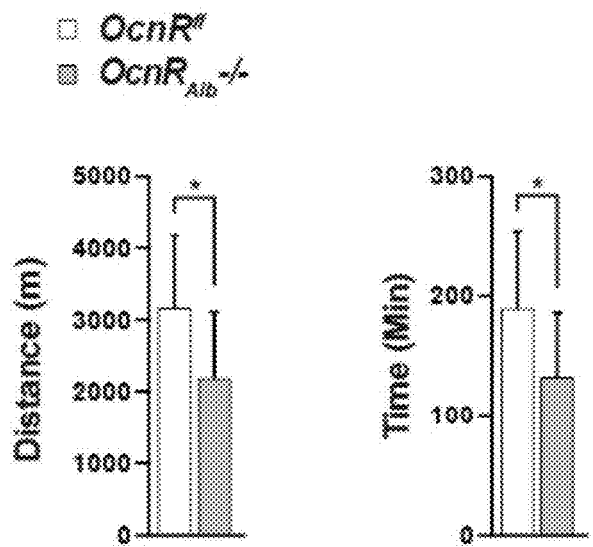
FIG. 6 is a set of exemplary graphs illustrating that OCN signaling in the liver is beneficial for exercise capacity.
Figure 7:
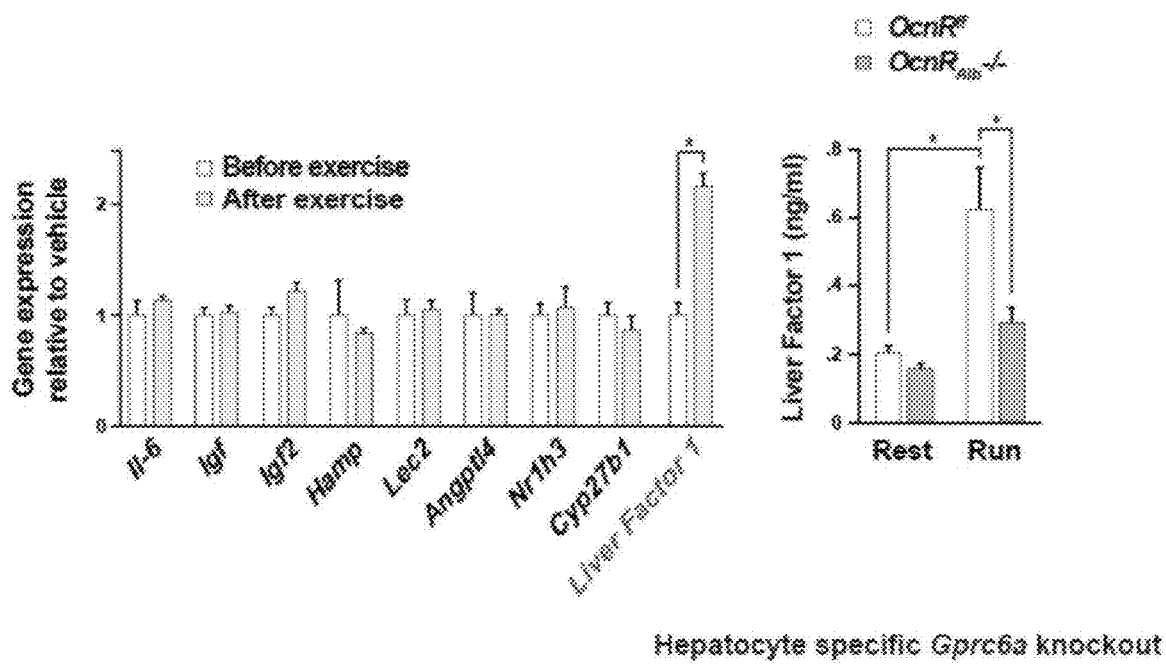
FIG. 7 is a set of exemplary graphs illustrating that OCN enhances Liver Factor 1 production during exercise.
Figure 8:
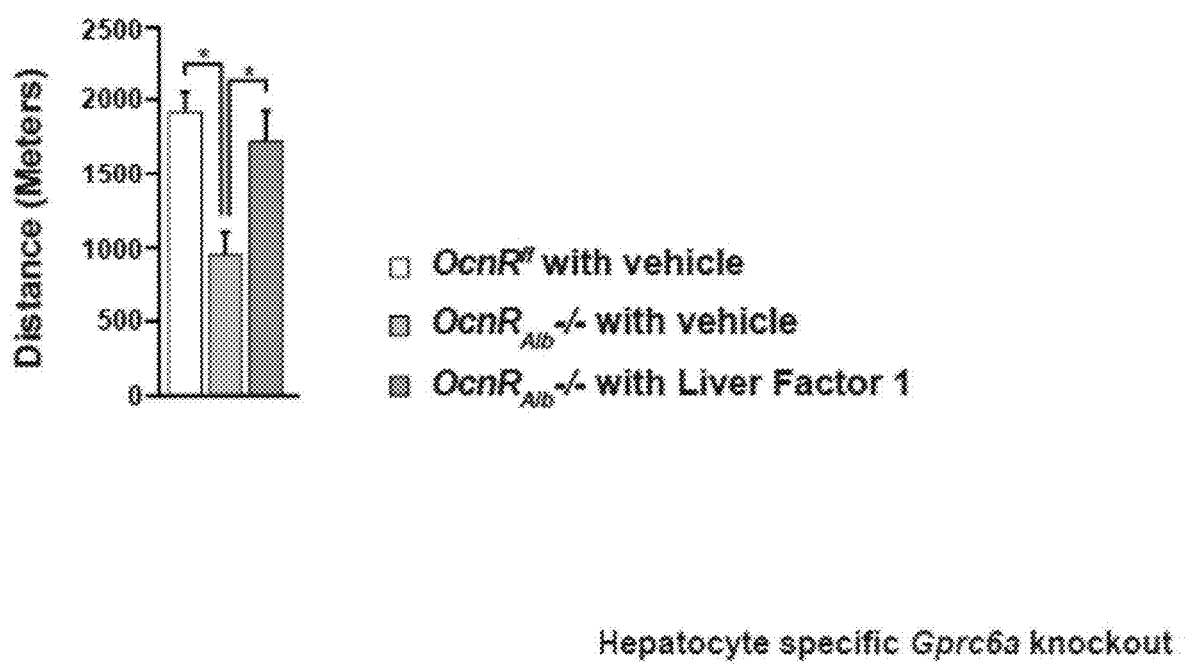
FIG. 8 is a set of exemplary graphs illustrating that Liver Factor 1 mediates OCN regulation of exercise capacity.

OCN signaling in the liver is required for exercise capacity (see FIG. 6). OCN enhances Liver Factor 1 production during exercise (see FIG. 7). Liver Factor 1 mediates OCN regulation of exercise capacity (see FIG. 8).

Example 3

Figure 9A:
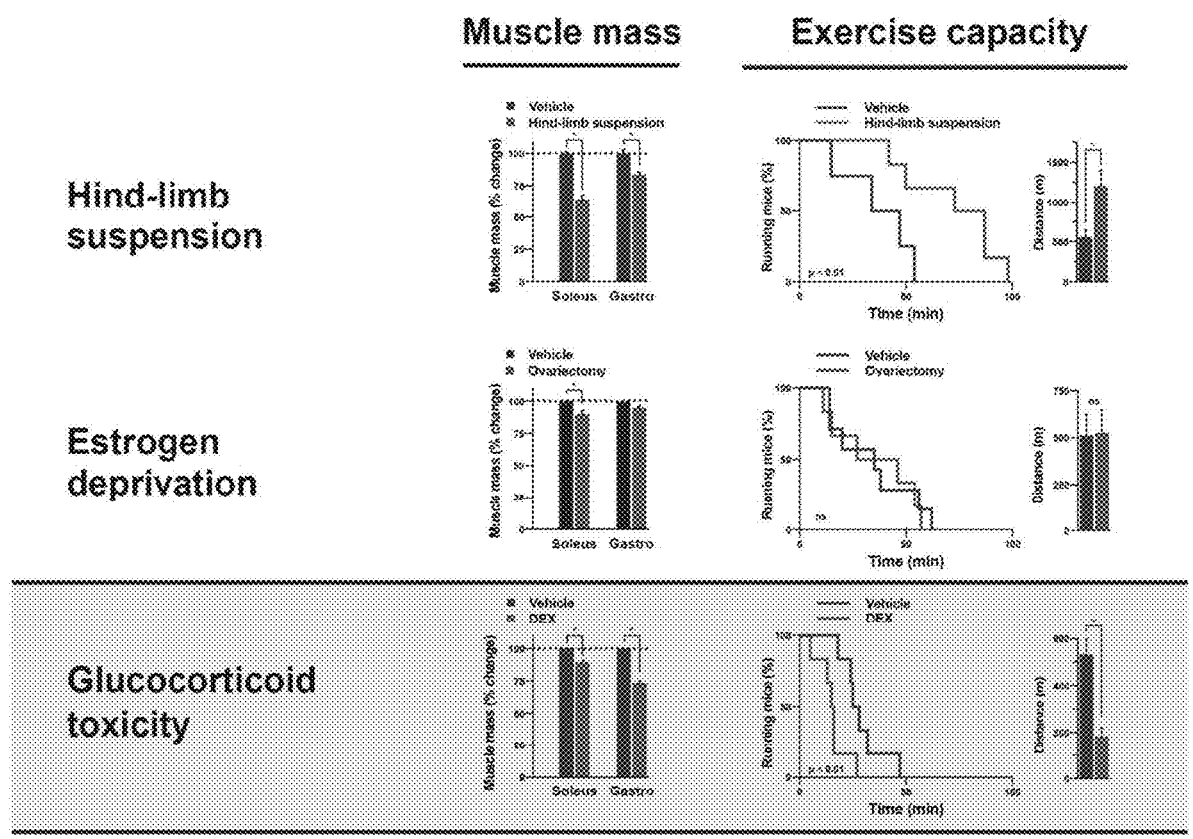
FIG. 9A and FIG. 9B are exemplary graphs illustrating exemplary modeling sarcopenia in mice.
Figure 9B:
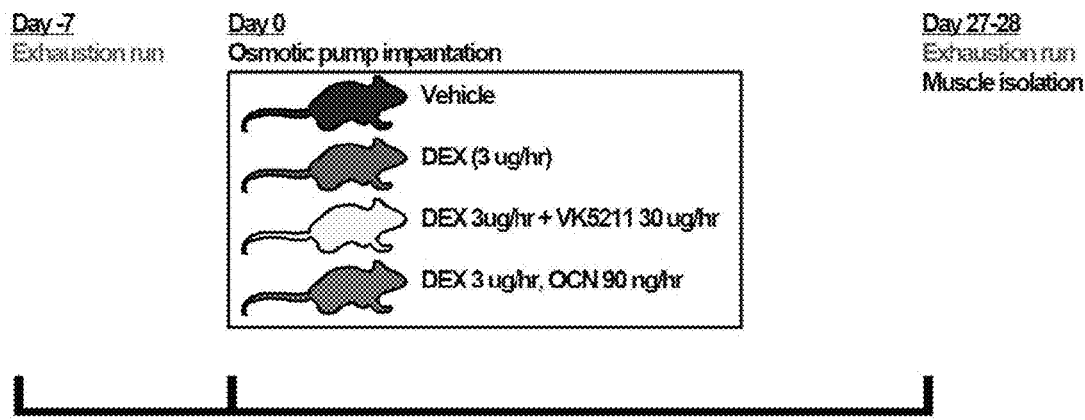

For example, a clinically relevant mouse model of sarcopenia has been identified and used to compare OCN and VK5211 efficacy in muscle mass and exercise capacity. FIG. 9A and FIG. 9B show exemplary graphs pf exemplary modeling sarcopenia in mice. This exemplary mouse model of dexamethasone (DEX)-induced sarcopenia is a model that exhibits both loss of muscle mass and function, reproduces the pathology and symptoms of Cushing's syndrome, and shares a common molecular pathway with many other forms of sarcopenia.

Figure 10:
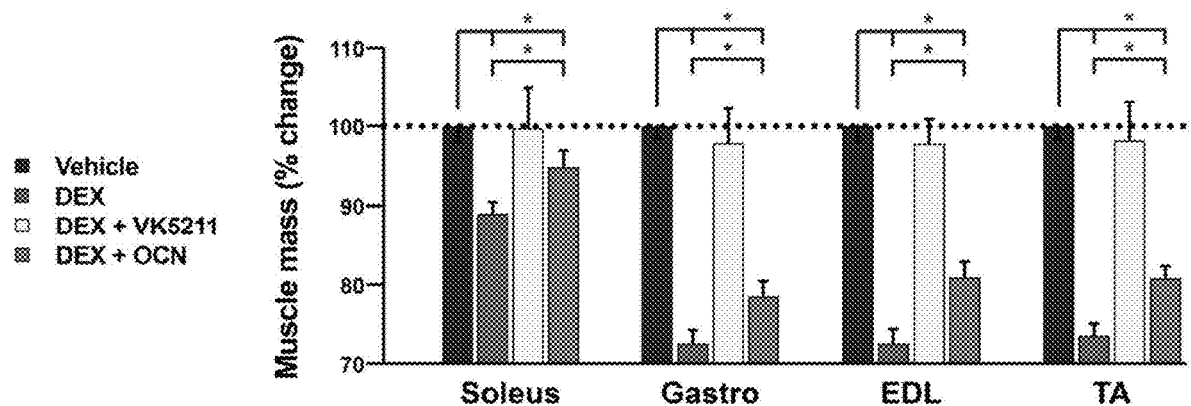
FIG. 10 is a set of exemplary graphs illustrating that OCN has a marginal effect on muscle mass in DEX sarcopenia.
Figure 11:
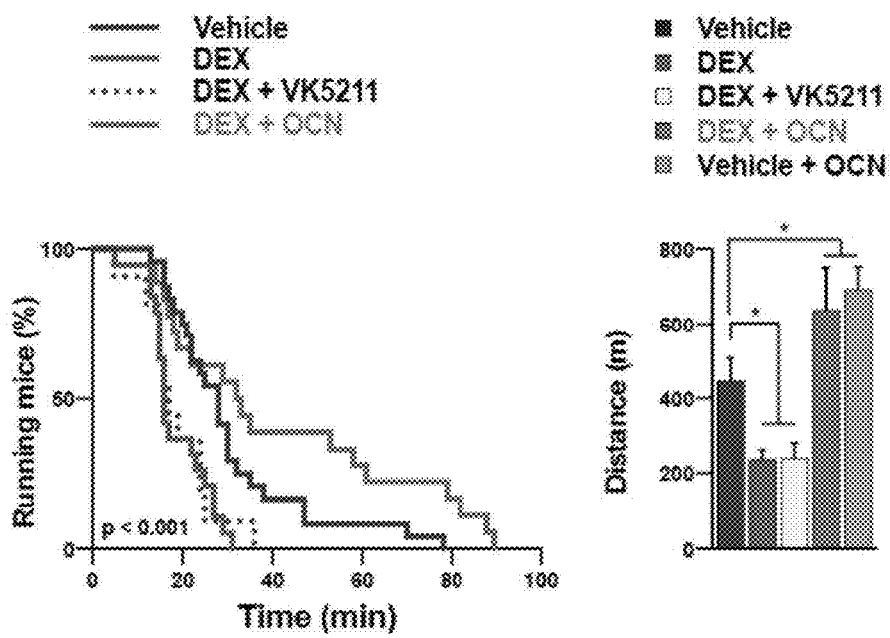
FIG. 11 is a set of exemplary graphs illustrating that OCN substantially or fully prevents DEX deleterious effect on exercise.
Figure 12:
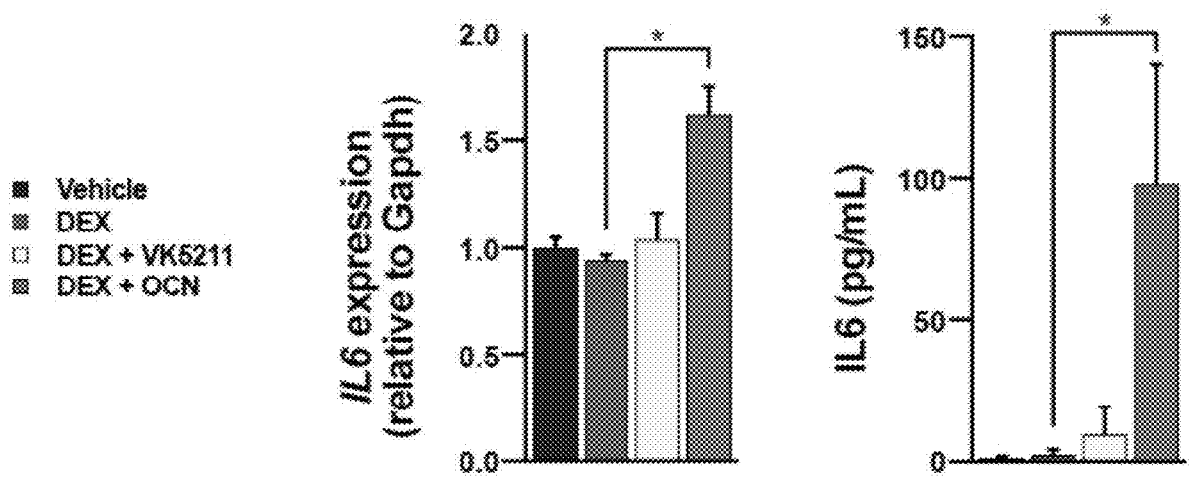
FIG. 12 is a set of exemplary graphs illustrating that OCN favors IL-6 in Dex-induced sarcopenia.
Figure 13:
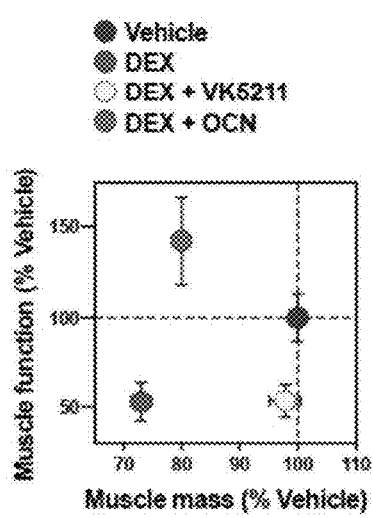
FIG. 13 is a set of exemplary graphs illustrating that OCN mainly targets muscle function.
Figure 14:
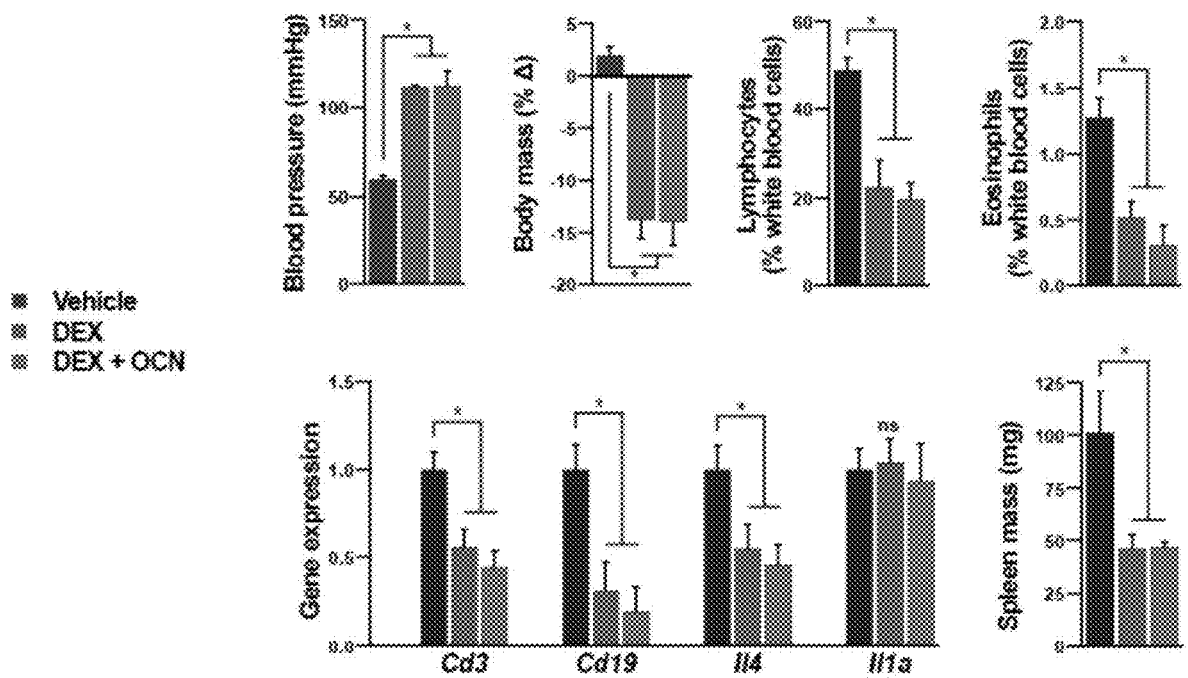
FIG. 14 is a set of exemplary graphs illustrating that OCN does not interfere with DEX toxicity.

OCN has a marginal effect on muscle mass in DEX sarcopenia (see FIG. 10) but fully prevents DEX deleterious effect on exercise (see FIG. 11). OCN favors IL-6 in Dex-induced sarcopenia (see FIG. 12). OCN mainly targets muscle function (see FIG. 13). OCN does not interfere with DEX toxicity (see FIG. 14).

Such exemplary results indicate that Osteocalcin coordinates the dynamic systemic response to exercise. Osteocalcin is the first molecule that targets loss of muscle function in Dex-induced sarcopenia. Osteocalcin outperforms a late stage clinical candidate, VK5211. Further, Osteocalcin has no overt off-target effects.

The foregoing merely illustrates the principles of the disclosure. Various modifications and alterations to the described embodiments will be apparent to those skilled in the art in view of the teachings herein. It will thus be appreciated that those skilled in the art will be able to devise numerous systems, arrangements, and procedures which, although not explicitly shown or described herein, embody the principles of the disclosure and can be thus within the spirit and scope of the disclosure. Various different exemplary embodiments can be used together with one another, as well as interchangeably therewith, as should be understood by those having ordinary skill in the art. In addition, certain terms used in the present disclosure, including the specification, drawings and claims thereof, can be used synonymously in certain instances, including, but not limited to, for example, data and information. It should be understood that, while these words, and/or other words that can be synonymous to one another, can be used synonymously herein, that there can be instances when such words can be intended to not be used synonymously. Further, to the extent that the prior art knowledge has not been explicitly incorporated by reference herein above, it is explicitly incorporated herein in its entirety. All publications referenced are incorporated herein by reference in their entireties.

What is claimed is:

1. A method for reducing loss of muscle function in a subject with sarcopenia, comprising: administering to the subject a pharmaceutical composition which comprises a therapeutically effective amount of Interleukin-6-Bisphosphonate fusion peptide.

2. The method of claim 1, wherein the subject is a human.

3. The method of claim 1, wherein the Interleukin-6-Bisphosphonate fusion peptide further reduces loss of muscle mass.

4. The method of claim 1, wherein the pharmaceutical composition further comprises a pharmaceutically acceptable carrier or excipient.

* * * * *

SEQUENCE LISTING

```
<160> NUMBER OF SEQ ID NOS: 38

<210> SEQ ID NO 1
<211> LENGTH: 42
<212> TYPE: PRT
<213> ORGANISM: Homo sapiens

<400> SEQUENCE: 1

Tyr Leu Tyr Gln Trp Leu Gly Ala Pro Val Pro Tyr Pro Asp Pro Leu
1               5                   10                  15

Glu Pro Arg Arg Glu Val Cys Glu Leu Asn Pro Asp Cys Asp Glu Leu
            20                  25                  30

Ala Asp His Ile Gly Phe Gln Glu Ala Tyr
        35                  40

<210> SEQ ID NO 2
<211> LENGTH: 44
<212> TYPE: PRT
<213> ORGANISM: Homo sapiens

<400> SEQUENCE: 2

Tyr Leu Tyr Gln Trp Leu Gly Ala Pro Val Pro Tyr Pro Asp Pro Leu
```

```
1               5                   10                  15
Glu Pro Arg Arg Glu Val Cys Glu Leu Asn Pro Asp Cys Asp Glu Leu
            20                  25                  30

Ala Asp His Ile Gly Phe Gln Glu Ala Tyr Arg Arg
            35                  40
```

<210> SEQ ID NO 3
<211> LENGTH: 49
<212> TYPE: PRT
<213> ORGANISM: Homo sapiens

<400> SEQUENCE: 3

```
Tyr Leu Tyr Gln Trp Leu Ala Ala Pro Val Pro Tyr Pro Asp Pro Leu
1               5                   10                  15

Glu Pro Arg Arg Glu Val Cys Glu Leu Asn Pro Asp Cys Asp Glu Leu
            20                  25                  30

Ala Asp His Ile Gly Phe Gln Glu Ala Tyr Arg Arg Phe Tyr Gly Pro
            35                  40                  45

Val
```

<210> SEQ ID NO 4
<211> LENGTH: 49
<212> TYPE: PRT
<213> ORGANISM: Homo sapiens

<400> SEQUENCE: 4

```
Tyr Leu Tyr Gln Trp Leu Gly Ala Ala Val Pro Tyr Pro Asp Pro Leu
1               5                   10                  15

Glu Pro Arg Arg Glu Val Cys Glu Leu Asn Pro Asp Cys Asp Glu Leu
            20                  25                  30

Ala Asp His Ile Gly Phe Gln Glu Ala Tyr Arg Arg Phe Tyr Gly Pro
            35                  40                  45

Val
```

<210> SEQ ID NO 5
<211> LENGTH: 49
<212> TYPE: PRT
<213> ORGANISM: Homo sapiens

<400> SEQUENCE: 5

```
Tyr Leu Tyr Gln Trp Leu Gly Ala Pro Ala Pro Tyr Pro Asp Pro Leu
1               5                   10                  15

Glu Pro Arg Arg Glu Val Cys Glu Leu Asn Pro Asp Cys Asp Glu Leu
            20                  25                  30

Ala Asp His Ile Gly Phe Gln Glu Ala Tyr Arg Arg Phe Tyr Gly Pro
            35                  40                  45

Val
```

<210> SEQ ID NO 6
<211> LENGTH: 49
<212> TYPE: PRT
<213> ORGANISM: Homo sapiens

<400> SEQUENCE: 6

```
Tyr Leu Tyr Gln Trp Leu Gly Ala Pro Val Ala Tyr Pro Asp Pro Leu
1               5                   10                  15

Glu Pro Arg Arg Glu Val Cys Glu Leu Asn Pro Asp Cys Asp Glu Leu
            20                  25                  30
```

Ala Asp His Ile Gly Phe Gln Glu Ala Tyr Arg Arg Phe Tyr Gly Pro
            35                  40                  45

Val

<210> SEQ ID NO 7
<211> LENGTH: 49
<212> TYPE: PRT
<213> ORGANISM: Homo sapiens

<400> SEQUENCE: 7

Tyr Leu Tyr Gln Trp Leu Gly Ala Pro Val Pro Ala Pro Asp Pro Leu
1               5                   10                  15

Glu Pro Arg Arg Glu Val Cys Glu Leu Asn Pro Asp Cys Asp Glu Leu
            20                  25                  30

Ala Asp His Ile Gly Phe Gln Glu Ala Tyr Arg Arg Phe Tyr Gly Pro
            35                  40                  45

Val

<210> SEQ ID NO 8
<211> LENGTH: 49
<212> TYPE: PRT
<213> ORGANISM: Homo sapiens

<400> SEQUENCE: 8

Tyr Leu Tyr Gln Trp Leu Gly Ala Pro Val Pro Tyr Ala Asp Pro Leu
1               5                   10                  15

Glu Pro Arg Arg Glu Val Cys Glu Leu Asn Pro Asp Cys Asp Glu Leu
            20                  25                  30

Ala Asp His Ile Gly Phe Gln Glu Ala Tyr Arg Arg Phe Tyr Gly Pro
            35                  40                  45

Val

<210> SEQ ID NO 9
<211> LENGTH: 49
<212> TYPE: PRT
<213> ORGANISM: Homo sapiens

<400> SEQUENCE: 9

Tyr Leu Tyr Gln Trp Leu Gly Ala Pro Val Pro Tyr Pro Ala Pro Leu
1               5                   10                  15

Glu Pro Arg Arg Glu Val Cys Glu Leu Asn Pro Asp Cys Asp Glu Leu
            20                  25                  30

Ala Asp His Ile Gly Phe Gln Glu Ala Tyr Arg Arg Phe Tyr Gly Pro
            35                  40                  45

Val

<210> SEQ ID NO 10
<211> LENGTH: 49
<212> TYPE: PRT
<213> ORGANISM: Homo sapiens

<400> SEQUENCE: 10

Tyr Leu Tyr Gln Trp Leu Gly Ala Pro Val Pro Tyr Pro Asp Ala Leu
1               5                   10                  15

Glu Pro Arg Arg Glu Val Cys Glu Leu Asn Pro Asp Cys Asp Glu Leu
            20                  25                  30

Ala Asp His Ile Gly Phe Gln Glu Ala Tyr Arg Arg Phe Tyr Gly Pro
            35                  40                  45

Val

<210> SEQ ID NO 11
<211> LENGTH: 49
<212> TYPE: PRT
<213> ORGANISM: Homo sapiens

<400> SEQUENCE: 11

Tyr Leu Tyr Gln Trp Leu Gly Ala Pro Val Pro Tyr Pro Asp Pro Ala
1               5                   10                  15

Glu Pro Arg Arg Glu Val Cys Glu Leu Asn Pro Asp Cys Asp Glu Leu
            20                  25                  30

Ala Asp His Ile Gly Phe Gln Glu Ala Tyr Arg Arg Phe Tyr Gly Pro
        35                  40                  45

Val

<210> SEQ ID NO 12
<211> LENGTH: 44
<212> TYPE: PRT
<213> ORGANISM: Homo sapiens

<400> SEQUENCE: 12

Tyr Leu Tyr Gln Trp Leu Ala Ala Pro Val Pro Tyr Pro Asp Pro Leu
1               5                   10                  15

Glu Pro Arg Arg Glu Val Cys Glu Leu Asn Pro Asp Cys Asp Glu Leu
            20                  25                  30

Ala Asp His Ile Gly Phe Gln Glu Ala Tyr Arg Arg
        35                  40

<210> SEQ ID NO 13
<211> LENGTH: 44
<212> TYPE: PRT
<213> ORGANISM: Homo sapiens

<400> SEQUENCE: 13

Tyr Leu Tyr Gln Trp Leu Gly Ala Ala Val Pro Tyr Pro Asp Pro Leu
1               5                   10                  15

Glu Pro Arg Arg Glu Val Cys Glu Leu Asn Pro Asp Cys Asp Glu Leu
            20                  25                  30

Ala Asp His Ile Gly Phe Gln Glu Ala Tyr Arg Arg
        35                  40

<210> SEQ ID NO 14
<211> LENGTH: 44
<212> TYPE: PRT
<213> ORGANISM: Homo sapiens

<400> SEQUENCE: 14

Tyr Leu Tyr Gln Trp Leu Gly Ala Pro Ala Pro Tyr Pro Asp Pro Leu
1               5                   10                  15

Glu Pro Arg Arg Glu Val Cys Glu Leu Asn Pro Asp Cys Asp Glu Leu
            20                  25                  30

Ala Asp His Ile Gly Phe Gln Glu Ala Tyr Arg Arg
        35                  40

<210> SEQ ID NO 15
<211> LENGTH: 44
<212> TYPE: PRT
<213> ORGANISM: Homo sapiens

<400> SEQUENCE: 15

-continued

Tyr Leu Tyr Gln Trp Leu Gly Ala Pro Val Ala Tyr Pro Asp Pro Leu
1               5                   10                  15

Glu Pro Arg Arg Glu Val Cys Glu Leu Asn Pro Asp Cys Asp Glu Leu
            20                  25                  30

Ala Asp His Ile Gly Phe Gln Glu Ala Tyr Arg Arg
        35                  40

<210> SEQ ID NO 16
<211> LENGTH: 44
<212> TYPE: PRT
<213> ORGANISM: Homo sapiens

<400> SEQUENCE: 16

Tyr Leu Tyr Gln Trp Leu Gly Ala Pro Val Pro Ala Pro Asp Pro Leu
1               5                   10                  15

Glu Pro Arg Arg Glu Val Cys Glu Leu Asn Pro Asp Cys Asp Glu Leu
            20                  25                  30

Ala Asp His Ile Gly Phe Gln Glu Ala Tyr Arg Arg
        35                  40

<210> SEQ ID NO 17
<211> LENGTH: 44
<212> TYPE: PRT
<213> ORGANISM: Homo sapiens

<400> SEQUENCE: 17

Tyr Leu Tyr Gln Trp Leu Gly Ala Pro Val Pro Tyr Ala Asp Pro Leu
1               5                   10                  15

Glu Pro Arg Arg Glu Val Cys Glu Leu Asn Pro Asp Cys Asp Glu Leu
            20                  25                  30

Ala Asp His Ile Gly Phe Gln Glu Ala Tyr Arg Arg
        35                  40

<210> SEQ ID NO 18
<211> LENGTH: 44
<212> TYPE: PRT
<213> ORGANISM: Homo sapiens

<400> SEQUENCE: 18

Tyr Leu Tyr Gln Trp Leu Gly Ala Pro Val Pro Tyr Pro Ala Pro Leu
1               5                   10                  15

Glu Pro Arg Arg Glu Val Cys Glu Leu Asn Pro Asp Cys Asp Glu Leu
            20                  25                  30

Ala Asp His Ile Gly Phe Gln Glu Ala Tyr Arg Arg
        35                  40

<210> SEQ ID NO 19
<211> LENGTH: 44
<212> TYPE: PRT
<213> ORGANISM: Homo sapiens

<400> SEQUENCE: 19

Tyr Leu Tyr Gln Trp Leu Gly Ala Pro Val Pro Tyr Pro Asp Ala Leu
1               5                   10                  15

Glu Pro Arg Arg Glu Val Cys Glu Leu Asn Pro Asp Cys Asp Glu Leu
            20                  25                  30

Ala Asp His Ile Gly Phe Gln Glu Ala Tyr Arg Arg
        35                  40

```
<210> SEQ ID NO 20
<211> LENGTH: 44
<212> TYPE: PRT
<213> ORGANISM: Homo sapiens

<400> SEQUENCE: 20

Tyr Leu Tyr Gln Trp Leu Gly Ala Pro Val Pro Tyr Pro Asp Pro Ala
1               5                   10                  15

Glu Pro Arg Arg Glu Val Cys Glu Leu Asn Pro Asp Cys Asp Glu Leu
            20                  25                  30

Ala Asp His Ile Gly Phe Gln Glu Ala Tyr Arg Arg
        35                  40

<210> SEQ ID NO 21
<211> LENGTH: 42
<212> TYPE: PRT
<213> ORGANISM: Homo sapiens

<400> SEQUENCE: 21

Tyr Leu Tyr Gln Trp Leu Ala Ala Pro Val Pro Tyr Pro Asp Pro Leu
1               5                   10                  15

Glu Pro Arg Arg Glu Val Cys Glu Leu Asn Pro Asp Cys Asp Glu Leu
            20                  25                  30

Ala Asp His Ile Gly Phe Gln Glu Ala Tyr
        35                  40

<210> SEQ ID NO 22
<211> LENGTH: 42
<212> TYPE: PRT
<213> ORGANISM: Homo sapiens

<400> SEQUENCE: 22

Tyr Leu Tyr Gln Trp Leu Gly Ala Ala Val Pro Tyr Pro Asp Pro Leu
1               5                   10                  15

Glu Pro Arg Arg Glu Val Cys Glu Leu Asn Pro Asp Cys Asp Glu Leu
            20                  25                  30

Ala Asp His Ile Gly Phe Gln Glu Ala Tyr
        35                  40

<210> SEQ ID NO 23
<211> LENGTH: 42
<212> TYPE: PRT
<213> ORGANISM: Homo sapiens

<400> SEQUENCE: 23

Tyr Leu Tyr Gln Trp Leu Gly Ala Pro Ala Pro Tyr Pro Asp Pro Leu
1               5                   10                  15

Glu Pro Arg Arg Glu Val Cys Glu Leu Asn Pro Asp Cys Asp Glu Leu
            20                  25                  30

Ala Asp His Ile Gly Phe Gln Glu Ala Tyr
        35                  40

<210> SEQ ID NO 24
<211> LENGTH: 42
<212> TYPE: PRT
<213> ORGANISM: Homo sapiens

<400> SEQUENCE: 24

Tyr Leu Tyr Gln Trp Leu Gly Ala Pro Val Ala Tyr Pro Asp Pro Leu
1               5                   10                  15

Glu Pro Arg Arg Glu Val Cys Glu Leu Asn Pro Asp Cys Asp Glu Leu
```

```
                    20                  25                  30

Ala Asp His Ile Gly Phe Gln Glu Ala Tyr
        35                  40

<210> SEQ ID NO 25
<211> LENGTH: 42
<212> TYPE: PRT
<213> ORGANISM: Homo sapiens

<400> SEQUENCE: 25

Tyr Leu Tyr Gln Trp Leu Gly Ala Pro Val Pro Ala Pro Asp Pro Leu
1               5                   10                  15

Glu Pro Arg Arg Glu Val Cys Glu Leu Asn Pro Asp Cys Asp Glu Leu
            20                  25                  30

Ala Asp His Ile Gly Phe Gln Glu Ala Tyr
        35                  40

<210> SEQ ID NO 26
<211> LENGTH: 42
<212> TYPE: PRT
<213> ORGANISM: Homo sapiens

<400> SEQUENCE: 26

Tyr Leu Tyr Gln Trp Leu Gly Ala Pro Val Pro Tyr Ala Asp Pro Leu
1               5                   10                  15

Glu Pro Arg Arg Glu Val Cys Glu Leu Asn Pro Asp Cys Asp Glu Leu
            20                  25                  30

Ala Asp His Ile Gly Phe Gln Glu Ala Tyr
        35                  40

<210> SEQ ID NO 27
<211> LENGTH: 42
<212> TYPE: PRT
<213> ORGANISM: Homo sapiens

<400> SEQUENCE: 27

Tyr Leu Tyr Gln Trp Leu Gly Ala Pro Val Pro Tyr Pro Ala Pro Leu
1               5                   10                  15

Glu Pro Arg Arg Glu Val Cys Glu Leu Asn Pro Asp Cys Asp Glu Leu
            20                  25                  30

Ala Asp His Ile Gly Phe Gln Glu Ala Tyr
        35                  40

<210> SEQ ID NO 28
<211> LENGTH: 42
<212> TYPE: PRT
<213> ORGANISM: Homo sapiens

<400> SEQUENCE: 28

Tyr Leu Tyr Gln Trp Leu Gly Ala Pro Val Pro Tyr Pro Asp Ala Leu
1               5                   10                  15

Glu Pro Arg Arg Glu Val Cys Glu Leu Asn Pro Asp Cys Asp Glu Leu
            20                  25                  30

Ala Asp His Ile Gly Phe Gln Glu Ala Tyr
        35                  40

<210> SEQ ID NO 29
<211> LENGTH: 42
<212> TYPE: PRT
<213> ORGANISM: Homo sapiens
```

-continued

<400> SEQUENCE: 29

Tyr Leu Tyr Gln Trp Leu Gly Ala Pro Val Pro Tyr Pro Asp Pro Ala
1               5                   10                  15

Glu Pro Arg Arg Glu Val Cys Glu Leu Asn Pro Asp Cys Asp Glu Leu
            20                  25                  30

Ala Asp His Ile Gly Phe Gln Glu Ala Tyr
        35                  40

<210> SEQ ID NO 30
<211> LENGTH: 281
<212> TYPE: PRT
<213> ORGANISM: Homo sapiens

<400> SEQUENCE: 30

Glu Pro Lys Ser Cys Asp Lys Thr His Thr Cys Pro Pro Cys Pro Ala
1               5                   10                  15

Pro Glu Ala Ala Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Cys Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys Tyr Leu Tyr Gln Trp Leu Gly Ala
225                 230                 235                 240

Pro Val Pro Tyr Pro Asp Pro Leu Glu Pro Arg Arg Glu Val Cys Glu
                245                 250                 255

Leu Asn Pro Asp Cys Asp Glu Leu Ala Asp His Ile Gly Phe Gln Glu
            260                 265                 270

Ala Tyr Arg Arg Phe Tyr Gly Pro Val
        275                 280

<210> SEQ ID NO 31
<211> LENGTH: 281
<212> TYPE: PRT
<213> ORGANISM: Homo sapiens

<400> SEQUENCE: 31

```
Tyr Leu Tyr Gln Trp Leu Gly Ala Pro Val Pro Tyr Pro Asp Pro Leu
1               5                   10                  15
Glu Pro Arg Arg Glu Val Cys Glu Leu Asn Pro Asp Cys Asp Glu Leu
            20                  25                  30
Ala Asp His Ile Gly Phe Gln Glu Ala Tyr Arg Arg Phe Tyr Gly Pro
        35                  40                  45
Val Glu Pro Lys Ser Cys Asp Lys Thr His Thr Cys Pro Pro Cys Pro
    50                  55                  60
Ala Pro Glu Ala Ala Gly Gly Pro Ser Val Phe Leu Phe Pro Pro Lys
65                  70                  75                  80
Pro Lys Asp Thr Leu Met Ile Ser Arg Thr Pro Glu Val Thr Cys Val
                85                  90                  95
Val Val Cys Val Ser His Glu Asp Pro Glu Val Lys Phe Asn Trp Tyr
            100                 105                 110
Val Asp Gly Val Glu Val His Asn Ala Lys Thr Lys Pro Arg Glu Glu
        115                 120                 125
Gln Tyr Asn Ser Thr Tyr Arg Val Val Ser Val Leu Thr Val Leu His
    130                 135                 140
Gln Asp Trp Leu Asn Gly Lys Glu Tyr Lys Cys Lys Val Ser Asn Lys
145                 150                 155                 160
Ala Leu Pro Ala Pro Ile Glu Lys Thr Ile Ser Lys Ala Lys Gly Gln
                165                 170                 175
Pro Arg Glu Pro Gln Val Tyr Thr Leu Pro Pro Ser Arg Asp Glu Leu
            180                 185                 190
Thr Lys Asn Gln Val Ser Leu Thr Cys Leu Val Lys Gly Phe Tyr Pro
        195                 200                 205
Ser Asp Ile Ala Val Glu Trp Glu Ser Asn Gly Gln Pro Glu Asn Asn
    210                 215                 220
Tyr Lys Thr Thr Pro Pro Val Leu Asp Ser Asp Gly Ser Phe Phe Leu
225                 230                 235                 240
Tyr Ser Lys Leu Thr Val Asp Lys Ser Arg Trp Gln Gln Gly Asn Val
                245                 250                 255
Phe Ser Cys Ser Val Met His Glu Ala Leu His Asn His Tyr Thr Gln
            260                 265                 270
Lys Ser Leu Ser Leu Ser Pro Gly Lys
        275                 280
```

<210> SEQ ID NO 32
<211> LENGTH: 49
<212> TYPE: PRT
<213> ORGANISM: Homo sapiens

<400> SEQUENCE: 32

```
Tyr Leu Tyr Gln Trp Leu Gly Ala Pro Val Pro Tyr Pro Asp Pro Leu
1               5                   10                  15
Glu Pro Arg Arg Glu Val Cys Glu Leu Asn Pro Asp Cys Asp Glu Leu
            20                  25                  30
Ala Asp His Ile Gly Phe Gln Glu Ala Tyr Arg Arg Phe Tyr Gly Pro
        35                  40                  45
Val
```

<210> SEQ ID NO 33
<211> LENGTH: 100
<212> TYPE: PRT

<213> ORGANISM: Homo sapiens

<400> SEQUENCE: 33

```
Met Arg Ala Leu Thr Leu Leu Ala Leu Leu Ala Leu Ala Ala Leu Cys
1               5                   10                  15

Ile Ala Gly Gln Ala Gly Ala Lys Pro Ser Gly Ala Glu Ser Ser Lys
            20                  25                  30

Gly Ala Ala Phe Val Ser Lys Gln Glu Gly Ser Glu Val Val Lys Arg
        35                  40                  45

Pro Arg Arg Tyr Leu Tyr Gln Trp Leu Gly Ala Pro Val Pro Tyr Pro
    50                  55                  60

Asp Pro Leu Glu Pro Arg Arg Glu Val Cys Glu Leu Asn Pro Asp Cys
65                  70                  75                  80

Asp Glu Leu Ala Asp His Ile Gly Phe Gln Glu Ala Tyr Arg Arg Phe
                85                  90                  95

Tyr Gly Pro Val
            100
```

<210> SEQ ID NO 34
<211> LENGTH: 498
<212> TYPE: DNA
<213> ORGANISM: Homo sapiens

<400> SEQUENCE: 34

| | | |
|---|---|---|
| cgcagccacc gagacaccat gagagccctc acactcctcg ccctattggc cctggccgca | 60 |
| ctttgcatcg ctggccaggc aggtgcgaag cccagcggtg cagagtccag caaaggtgca | 120 |
| gcctttgtgt ccaagcagga gggcagcgag gtagtgaaga cccaggcg ctacctgtat | 180 |
| caatggctgg gagccccagt cccctacccg gatcccctgg agcccaggag ggaggtgtgt | 240 |
| gagctcaatc cggactgtga cgagttggct gaccacatcg gctttcagga ggcctatcgg | 300 |
| cgcttctacg gcccggtcta gggtgtcgct ctgctggcct ggccggcaac ccagttctg | 360 |
| ctcctctcca ggcacccttc tttcctcttc cccttgccct tgccctgacc tcccagccct | 420 |
| atggatgtgg ggtccccatc atcccagctg ctcccaaata aactccagaa gaggaatctg | 480 |
| aaaaaaaaaa aaaaaaaa | 498 |

<210> SEQ ID NO 35
<211> LENGTH: 494
<212> TYPE: DNA
<213> ORGANISM: Mus musculus

<400> SEQUENCE: 35

| | | |
|---|---|---|
| agaacagaca agtcccacac agcagcttgg cccagaccta gcagacacca tgaggaccat | 60 |
| ctttctgctc actctgctga ccctggctgc gctctgtctc tctgacctca cagatgccaa | 120 |
| gcccagcggc cctgagtctg acaaagcctt catgtccaag caggagggca ataaggtagt | 180 |
| gaacagactc cggcgctacc ttggagcct agtccccagc ccagatcccc tggagcccac | 240 |
| ccgggagcag tgtgagctta accctgcttg tgacgagcta tcagaccagt atggcttgaa | 300 |
| gaccgcctac aaacgcatct atggtatcac tatttaggac ctgtgctgcc ctaaagccaa | 360 |
| actctggcag ctcggctttg gctgctctcc gggacttgat cctccctgtc ctctctctct | 420 |
| gccctgcaag tatggatgtc acagcagctc caaaataaag ttcagatgag gaagtgcaaa | 480 |
| aaaaaaaaaa aaaa | 494 |

<210> SEQ ID NO 36

-continued

```
<211> LENGTH: 470
<212> TYPE: DNA
<213> ORGANISM: Mus musculus

<400> SEQUENCE: 36
gaacagacaa gtcccacaca gcagcttggt gcacacctag cagacaccat gaggaccctc      60
tctctgctca ctctgctggc cctggctgcg ctctgtctct ctgacctcac agatcccaag     120
cccagcggcc ctgagtctga caaagccttc atgtccaagc aggagggcaa taaggtagtg     180
aacagactcc ggcgctacct tggagcctca gtccccagcc cagatcccct ggagcccacc     240
cgggagcagt gtgagcttaa ccctgcttgt gacgagctat cagaccagta tggcttgaag     300
accgcctaca acgcatcta cggtatcact atttaggacc tgtgctgccc taaagccaaa     360
ctctggcagc tcggctttgg ctgctctccg ggacttgatc ctccctgtcc tctctctctg     420
ccctgcaagt atggatgtca cagcagctcc aaaataaagt tcagatgagg                470

<210> SEQ ID NO 37
<211> LENGTH: 95
<212> TYPE: PRT
<213> ORGANISM: Mus musculus

<400> SEQUENCE: 37

Met Arg Thr Leu Ser Leu Leu Thr Leu Leu Ala Leu Ala Ala Leu Cys
1               5                   10                  15

Leu Ser Asp Leu Thr Asp Pro Lys Pro Ser Gly Pro Glu Ser Asp Lys
                20                  25                  30

Ala Phe Met Ser Lys Gln Glu Gly Asn Lys Val Val Asn Arg Leu Arg
            35                  40                  45

Arg Tyr Leu Gly Ala Ser Val Pro Ser Pro Asp Pro Leu Glu Pro Thr
        50                  55                  60

Arg Glu Gln Cys Glu Leu Asn Pro Ala Cys Asp Glu Leu Ser Asp Gln
65                  70                  75                  80

Tyr Gly Leu Lys Thr Ala Tyr Lys Arg Ile Tyr Gly Ile Thr Ile
                85                  90                  95

<210> SEQ ID NO 38
<211> LENGTH: 49
<212> TYPE: PRT
<213> ORGANISM: Homo sapiens
<220> FEATURE:
<221> NAME/KEY: MISC_FEATURE
<222> LOCATION: (17)..(17)
<223> OTHER INFORMATION: Xaa can be any naturally occurring amino acid
<220> FEATURE:
<221> NAME/KEY: MISC_FEATURE
<222> LOCATION: (21)..(21)
<223> OTHER INFORMATION: Xaa can be any naturally occurring amino acid
<220> FEATURE:
<221> NAME/KEY: MISC_FEATURE
<222> LOCATION: (24)..(24)
<223> OTHER INFORMATION: Xaa can be any naturally occurring amino acid

<400> SEQUENCE: 38

Tyr Leu Tyr Gln Trp Leu Gly Ala Pro Val Pro Tyr Pro Asp Pro Leu
1               5                   10                  15

Xaa Pro Arg Arg Xaa Val Cys Xaa Leu Asn Pro Asp Cys Asp Glu Leu
                20                  25                  30

Ala Asp His Ile Gly Phe Gln Glu Ala Tyr Arg Arg Phe Tyr Gly Pro
            35                  40                  45

Val
```